United States Patent
Hansen et al.

(10) Patent No.: US 6,596,103 B1
(45) Date of Patent: *Jul. 22, 2003

(54) METHOD OF BINDING BINDER TREATED PARTICLES TO FIBERS

(75) Inventors: Michael R. Hansen, Seattle, WA (US); Richard H. Young, Sr., Renton, WA (US)

(73) Assignee: Weyerhaeuser Company, Federal Way, WA (US)

( * ) Notice: Subject to any disclaimer, the term of this patent is extended or adjusted under 35 U.S.C. 154(b) by 2 days.

This patent is subject to a terminal disclaimer.

(21) Appl. No.: 09/704,328

(22) Filed: Nov. 1, 2000

Related U.S. Application Data

(63) Continuation of application No. 08/791,335, filed on Jan. 31, 1997, now Pat. No. 6,461,553, which is a continuation of application No. 08/486,686, filed on Jun. 7, 1995, now abandoned, which is a division of application No. 08/108,218, filed on Aug. 17, 1993, now Pat. No. 5,641,561, which is a continuation-in-part of application No. 07/931,059, filed on Aug. 17, 1992, now Pat. No. 5,543,215, and a continuation-in-part of application No. 07/931,277, filed on Aug. 17, 1992, now Pat. No. 5,538,783, and a continuation-in-part of application No. 07/931,213, filed on Aug. 17, 1992, now Pat. No. 5,300,192, and a continuation-in-part of application No. 07/931,278, filed on Aug. 17, 1992, now Pat. No. 5,352,480, and a continuation-in-part of application No. 07/931,284, filed on Aug. 17, 1992, now Pat. No. 5,308,896, and a continuation-in-part of application No. 07/931,279, filed on Aug. 17, 1992, now Pat. No. 5,589,256.

(51) Int. Cl.$^7$ .............................................. B32B 31/00
(52) U.S. Cl. ...................... 156/62.2; 156/305; 156/326; 427/180; 162/135
(58) Field of Search ................................ 156/62.2, 305, 156/326; 428/420; 264/122; 162/135; 427/180

(56) References Cited

U.S. PATENT DOCUMENTS 2,601,597 A 6/1952 Daniel, Jr. et al.

(List continued on next page.)

FOREIGN PATENT DOCUMENTS

CA 729513 3/1966

(List continued on next page.)

OTHER PUBLICATIONS

Amosov et al., "Aluminum hydroxy compounds—binders for dry–process paper," *Izv. VUZ, Lesnoi Zh.*, 6:72–76 (1986).

Blanchard and Reinhart, "Dyeing of Crosslinked Cotton Containing Glycol Additives," *U.S. Dept. of Agriculture*, New Orleans, 24:13–17 (Jan. 1992).

(List continued on next page.)

*Primary Examiner*—Jeff H. Aftergut
(74) *Attorney, Agent, or Firm*—Christensen O'Connor Johnson Kindness PLLC

(57) ABSTRACT

A binder is applied to particles which are then combined with fibers to bind the particles to the fibers. The particles have functional sites for forming a hydrogen bond or a coordinate covalent bond. The fibers have hydrogen bonding functional sites. The binder comprises binder molecules, the binder molecules having at least one functional group that is capable of forming a hydrogen bond or a coordinate covalent bond with the particles, and at least one functional group that is capable of forming a hydrogen bond with the fibers. A substantial portion of the particles that are adhered to the fibers may be adhered in particulate form by hydrogen bonds or coordinate covalent bonds to the binder, and the binder in turn may be adhered to the fibers by hydrogen bonds. Fibers containing particles bound by this method are easily densified.

30 Claims, 8 Drawing Sheets

U.S. PATENT DOCUMENTS

| | | |
|---|---|---|
| RE24,011 E | 5/1955 | Ericks |
| 2,849,000 A | 8/1958 | Lewing |
| 2,953,187 A | 9/1960 | Francis, Jr. |
| 3,010,161 A | 11/1961 | Duvall |
| 3,059,313 A | 10/1962 | Harmon |
| 3,021,242 A | 12/1962 | Touey |
| 3,070,095 A | 12/1962 | Torr |
| 3,087,833 A | 4/1963 | Drelich |
| 3,327,708 A | 6/1967 | Sokolowski |
| 3,344,789 A | 10/1967 | Arnold et al. |
| 3,350,486 A | 10/1967 | Knoepfler et al. |
| 3,371,666 A | 3/1968 | Lewing |
| 3,377,302 A | 4/1968 | Gugliemelli et al. |
| 3,395,201 A | 7/1968 | Kalwaites |
| 3,409,497 A | 11/1968 | Roseland |
| 3,425,971 A | 2/1969 | Gugliemelli et al. |
| 3,494,992 A | 2/1970 | Wiegand |
| 3,521,638 A | 7/1970 | Parrish |
| 3,554,788 A | 1/1971 | Fechillas |
| 3,645,836 A | 2/1972 | Torr |
| 3,661,154 A | 5/1972 | Torr |
| 3,661,632 A | 5/1972 | Gagliardi et al. |
| 3,669,103 A | 6/1972 | Harper et al. |
| 3,670,731 A | 6/1972 | Harmon |
| 3,672,945 A | 6/1972 | Taylor |
| 3,686,024 A | 8/1972 | Nankee et al. |
| 3,692,622 A | 9/1972 | Dunning |
| 3,745,060 A | 7/1973 | Jumentier et al. |
| 3,758,641 A | 9/1973 | Zweigle |
| 3,766,922 A | 10/1973 | Krusko |
| 3,777,758 A | 12/1973 | Mesek et al. |
| 3,788,936 A | 1/1974 | Brock et al. |
| 3,804,092 A | 4/1974 | Tunc |
| 3,808,088 A | 4/1974 | Knechtges et al. |
| 3,886,941 A | 6/1975 | Duane et al. |
| 3,888,256 A | 6/1975 | Studinger |
| 3,888,257 A | 6/1975 | Cook et al. |
| 3,901,236 A | 8/1975 | Assarsson et al. |
| 3,903,889 A | 9/1975 | Torr |
| 3,908,659 A | 9/1975 | Wehrmeyer et al. |
| 3,923,592 A | 12/1975 | George et al. |
| 3,949,035 A | 4/1976 | Dunning et al. |
| 3,959,569 A | 5/1976 | Burkholder, Jr. |
| 3,978,257 A | 8/1976 | Ring |
| 3,991,237 A | 11/1976 | Topfl et al. |
| 4,007,083 A | 2/1977 | Ring et al. |
| 4,009,313 A | 2/1977 | Crawford et al. |
| 4,035,217 A | 7/1977 | Kennette et al. |
| 4,051,086 A | 9/1977 | Reid |
| 4,055,180 A | 10/1977 | Karami |
| 4,061,268 A | 12/1977 | DeMaster |
| 4,062,451 A | 12/1977 | Gander |
| 4,066,583 A | 1/1978 | Spaulding |
| 4,071,636 A | 1/1978 | Nishino et al. |
| 4,096,312 A | 6/1978 | Holst et al. |
| 4,102,340 A | 7/1978 | Mesek et al. |
| 4,103,062 A | 7/1978 | Aberson et al. |
| 4,128,692 A | 12/1978 | Reid |
| 4,160,059 A | 7/1979 | Samejima |
| 4,232,674 A | 11/1980 | Melican |
| 4,235,237 A | 11/1980 | Mesek et al. |
| 4,250,660 A | 2/1981 | Kitamura et al. |
| 4,282,121 A | 8/1981 | Goodrich |
| 4,289,513 A | 9/1981 | Brownhill et al. |
| 4,289,536 A | 9/1981 | Dereser |
| 4,324,706 A | 4/1982 | Tabe et al. |
| 4,332,917 A | 6/1982 | Heslinga et al. |
| 4,337,111 A | 6/1982 | Kaufman et al. |
| 4,338,417 A | 7/1982 | Heslinga et al. |
| 4,354,487 A | 10/1982 | Oczkowski et al. |
| 4,364,992 A | 12/1982 | Ito et al. |
| 4,379,194 A | 4/1983 | Clarke et al. |
| 4,392,908 A | 7/1983 | Dehnel |
| 4,394,172 A | 7/1983 | Scheuble et al. |
| 4,404,250 A | 9/1983 | Clarke |
| 4,410,571 A | 10/1983 | Korpman |
| 4,412,036 A | 10/1983 | Pederson et al. |
| 4,415,388 A | 11/1983 | Korpman |
| 4,424,247 A | 1/1984 | Erickson |
| 4,444,830 A | 4/1984 | Erickson |
| 4,457,978 A | 7/1984 | Wawzonek |
| 4,467,012 A | 8/1984 | Pederson et al. |
| 4,481,076 A | 11/1984 | Herrick |
| 4,486,501 A | 12/1984 | Holbek |
| 4,492,729 A | 1/1985 | Bannerman et al. |
| 4,500,315 A | 2/1985 | Pieniak et al. |
| 4,507,438 A | 3/1985 | Obayashi et al. |
| 4,532,176 A | 7/1985 | Briggs et al. |
| 4,537,767 A | 8/1985 | Rothman et al. |
| 4,541,871 A | 9/1985 | Obayashi et al. |
| 4,552,816 A | 11/1985 | Spahic et al. |
| 4,558,091 A | 12/1985 | Hubbard |
| 4,597,930 A | 7/1986 | Szal |
| 4,605,401 A | 8/1986 | Chmelir et al. |
| 4,610,678 A | 9/1986 | Weisman et al. |
| 4,666,975 A | 5/1987 | Yamasaki et al. |
| 4,666,983 A | 5/1987 | Tsubakimoto et al. |
| 4,673,402 A | 6/1987 | Weisman et al. |
| 4,676,784 A | 6/1987 | Erdman et al. |
| 4,685,909 A | 8/1987 | Berg et al. |
| 4,699,808 A * | 10/1987 | Menard et al. ............. 427/180 |
| 4,721,647 A | 1/1988 | Nakanishi et al. |
| 4,734,478 A | 3/1988 | Tsubakimoto |
| 4,755,178 A | 7/1988 | Insley et al. |
| 4,758,466 A | 7/1988 | Dabi et al. |
| 4,764,418 A | 8/1988 | Kuenn et al. |
| 4,772,492 A | 9/1988 | Bouchette |
| 4,788,080 A | 11/1988 | Hojo et al. |
| 4,798,744 A | 1/1989 | Goldstein et al. |
| 4,813,948 A | 3/1989 | Insley |
| 4,818,599 A | 4/1989 | Marcus |
| 4,824,689 A | 4/1989 | Kuenn et al. |
| 4,826,880 A | 5/1989 | Lesniak et al. |
| 4,833,011 A | 5/1989 | Horimoto |
| 4,842,593 A | 6/1989 | Jordan et al. |
| 4,851,069 A | 7/1989 | Packard et al. |
| 4,874,811 A | 10/1989 | Borchers et al. |
| 4,886,697 A | 12/1989 | Perdelwitz, Jr. et al. |
| 4,888,238 A | 12/1989 | Katz et al. |
| 4,892,769 A | 1/1990 | Perdelwitz, Jr. et al. |
| 4,902,559 A | 2/1990 | Eschwey et al. |
| 4,902,565 A | 2/1990 | Brook |
| 4,944,734 A | 7/1990 | Wallach |
| 4,990,551 A | 2/1991 | Haubl |
| 5,002,814 A | 3/1991 | Knack et al. |
| 5,002,986 A | 3/1991 | Fujiura et al. |
| 5,041,104 A | 8/1991 | Seal |
| 5,057,166 A | 10/1991 | Young, Sr. et al. |
| 5,064,689 A | 11/1991 | Young, Sr. et al. |
| 5,128,082 A | 7/1992 | Makoui |
| 5,149,334 A | 9/1992 | Lahrman et al. |
| 5,149,335 A | 9/1992 | Kellenberger et al. |
| 5,161,686 A | 11/1992 | Weber et al. |
| 5,217,445 A | 6/1993 | Young et al. |
| 5,217,576 A | 6/1993 | Van Phan |
| 5,225,047 A | 7/1993 | Graef et al. |
| 5,230,959 A | 7/1993 | Young, Sr. et al. |
| 5,240,562 A | 8/1993 | Phan et al. |
| 5,252,275 A | 10/1993 | Sultze et al. |
| 5,252,340 A | 10/1993 | Honeycutt |
| 5,264,082 A | 11/1993 | Phan et al. |

| | | | | | |
|---|---|---|---|---|---|
| 5,278,206 A | 1/1994 | Gobel et al. | FR | 2.080.724 | 2/1971 |
| 5,278,222 A | 1/1994 | Stack | GB | 260935 | 5/1926 |
| 5,283,123 A | 2/1994 | Carter et al. | GB | 720390 | 12/1954 |
| 5,294,249 A | 3/1994 | Luisi | GB | 1 217 452 | 12/1969 |
| 5,300,054 A | 4/1994 | Feist et al. | GB | 1331964 | 9/1973 |
| 5,300,192 A | 4/1994 | Hansen et al. | GB | 2 004 201 A | 3/1979 |
| 5,308,896 A | 5/1994 | Hansen et al. | GB | 2 007 998 A | 5/1979 |
| 5,312,522 A | 5/1994 | Van Phan et al. | GB | 2 092 895 A | 8/1982 |
| 5,352,480 A | 10/1994 | Hansen et al. | GB | 2119384 A | 11/1983 |
| 5,362,776 A | 11/1994 | Barenberg et al. | GB | 0 157 960 | 10/1985 |
| 5,378,528 A | 1/1995 | Makoui | GB | 2189127 | 10/1987 |
| 5,382,610 A | 1/1995 | Harada et al. | JP | 58-25499 | 5/1983 |
| 5,432,000 A | 7/1995 | Young, Sr. et al. | JP | 58183754 | 10/1983 |
| 5,447,977 A | 9/1995 | Hansen et al. | JP | 59-189103 | 10/1984 |
| 5,449,551 A | 9/1995 | Taniguchi | JP | 60-7490 | 2/1985 |
| 5,492,759 A | 2/1996 | Eriksson et al. | JP | Sho 61-28422 | 2/1986 |
| 5,498,478 A | 3/1996 | Hansen et al. | JP | 61272050 | 12/1986 |
| 5,516,569 A | 5/1996 | Veith et al. | JP | 61-282465 | 12/1986 |
| 5,538,783 A | 7/1996 | Hansen et al. | JP | 42994/88 | 2/1988 |
| 5,543,215 A | 8/1996 | Hansen et al. | JP | 63035803 | 2/1988 |
| 5,547,541 A | 8/1996 | Hansen et al. | JP | 1-156578 | 6/1989 |
| 5,547,745 A | 8/1996 | Hansen et al. | JP | 1-162874 | 6/1989 |
| 5,571,618 A | 11/1996 | Hansen et al. | JP | 1229881 | 9/1989 |
| 5,589,256 A | 12/1996 | Hansen et al. | JP | 1-282389 | 11/1989 |
| 5,597,873 A | 1/1997 | Chambers et al. | JP | 2530668 | 6/1996 |
| 5,607,759 A | 3/1997 | Hansen et al. | JP | 3016879 | 12/1999 |
| 5,609,727 A | 3/1997 | Hansen et al. | RU | 1390284 | 4/1988 |
| 5,611,885 A * | 3/1997 | Hansen et al. ............... 156/326 | WO | WO 88/01316 | 2/1988 |
| 5,614,570 A | 3/1997 | Hansen et al. | WO | WO 88/04704 | 6/1988 |
| 5,633,316 A | 5/1997 | Gartner et al. | WO | WO 88/07381 | 10/1988 |
| 5,641,561 A | 6/1997 | Hansen et al. | WO | WO 90/09236 | 8/1990 |
| 5,672,418 A | 9/1997 | Hansen et al. | WO | WO 90/11181 | 10/1990 |
| 5,693,411 A | 12/1997 | Hansen et al. | WO | WO 91/05108 | 4/1991 |
| 5,789,326 A | 8/1998 | Hansen et al. | WO | WO 91/09916 | 7/1991 |
| 5,807,364 A | 9/1998 | Hansen | WO | WO 91/10010 | 7/1991 |
| 5,851,672 A | 12/1998 | Wang et al. | WO | WO 93/24153 | 12/1993 |
| 5,994,440 A | 11/1999 | Staples et al. | WO | WO 94/04351 | 3/1994 |
| | | | WO | WO 94/04352 | 3/1994 |
| | FOREIGN PATENT DOCUMENTS | | WO | WO 95/00703 | 1/1995 |

| | | |
|---|---|---|
| CA | 806352 | 2/1969 |
| CA | 813616 | 5/1969 |
| CA | 841940 | 5/1970 |
| CA | 953 890 | 9/1974 |
| CA | 1052156 | 12/1976 |
| DE | 254357 | 7/1926 |
| DE | 489 308 | 1/1930 |
| DE | 1 079 796 | 6/1962 |
| DE | 2 048 721 | 6/1971 |
| DE | 29 49 531 A1 | 7/1980 |
| DE | 3313344 | 10/1984 |
| EP | 0 071 063 A1 | 2/1983 |
| EP | 0 096 976 A2 | 12/1983 |
| EP | 0 099 586 A3 | 2/1984 |
| EP | 0 122042 A2 | 10/1984 |
| EP | 0156649 A2 | 10/1985 |
| EP | 0 157 960 A1 | 10/1985 |
| EP | 0 210 754 A1 | 2/1987 |
| EP | 0233067 A2 | 9/1987 |
| EP | 0317106 A2 | 5/1989 |
| EP | 0402650 A2 | 12/1990 |
| EP | 0 427 316 A2 | 5/1991 |
| EP | 0 427 317 A2 | 5/1991 |
| EP | 0 429 112 A2 | 5/1991 |
| EP | 0 440 472 A1 | 8/1991 |
| EP | 0 442 185 A1 | 8/1991 |
| EP | 0450922 A2 | 10/1991 |
| EP | 0450923 A2 | 10/1991 |
| EP | 0450924 A2 | 10/1991 |
| EP | P 471 114 A2 | 2/1992 |
| EP | 0 509 708 A1 | 10/1992 |
| FR | 1 382 716 | 2/1964 |

OTHER PUBLICATIONS

Burkholder, "Absorbent Polymers—A New Concept in Fluid Absorption," *The Dow Chemical Company Designed Products Laboratory*, Midland, Michigan, pp. 73–79 (1973).

Byrd, "How bonds develop during web consolidation," *PTI*, pp. 240–243 (Oct. 1986).

Gorbushin et al., "Investigation of the effect of the nature and concentration of binders on the properties of dry–process paper," *Sb. Tr. Tsentr. Nauch.–Issled. Inst. Bumagi*, 9:117–123 (1974).

Gugliemelli et al., "Base–Hydrolyzed Starch–Polyacrylonitrile (S–PAN) Graft Copolymer. S–PAN–1:1, PAN M.W. 794,000*", *J. of Applied Copolymer Science*, 13:2007–2017 (1969).

Hoque et al., "Granulation and Tabletting of Iron Oxide–Chromic Oxide Catalyst Mass with the Aid of Binding Ingredients Part II–Cellulosic Derivatives and Polyethylene Glycol as Binding Ingredients," *Fertilizer Technology*, 20:30–35 (1983).

Lindsay, "Absorbent Starch Based Co–polymers—Their Characteristics and Applications," *Formed Fabrics Industry*, pp. 20, 24 and 26 (May 1977).

Lysogorskaya et al., "Effect of Moisture Content on the Development of Interfiber Bonds in Air–Laid Paper," *Leningrad Technological Institute of the Pulp and Paper Industry*, Zh. Prikl, Khim., 63:(8) 1869–1872 (1990).

Lysogorskaya et al., "Effect of Moisture Content on Development of Interfiber Bonding in the Structure of Air–Dried Paper," *Plenum Publ. Corp.*, pp. 1730–1733 (1991).

Ogurtsov et al., "Effect of the modulus of elasticity of the binder on the properties of dry–process paper," *Sb. Tr. Tsentr. Nauch.–Issled. Inst. Bumagi*, 9:123–127 (1974).

S. Lammie, "Use of Glycerine as a Softener for Paper Products," *The World's Paper Trade Review*, p. 2050, Dec. 13, 1962.

Sliwiok and Kowalska, "Investigation of Self–Association of the Selected Glycols and Cellulose Sorbents," Microchemical Journal, 26:68–74 (Jan. 1992).

"Super slurpers: Time for change?," *Chemical Week*, pp. 21–22 Jul. 24, 1974.

Weaver et al., "Hydrolyzed Starch–Polyacrylonitrile Graft Copolymers: Effect of Structure on Properties*", *J. of Applied Polymer Science*, 15:3015–3024 (1971).

Weaver et al., "Highly Absorbent Starch–Based Polymer," *Northern Regional Research Laboratory, Agricultural Research Service*, U.S. Dept. of Agriculture, Peoria, Illinois, pp. 169–177.

Neogi, A.N. et al., "Wet strength improvement via fiber surface modification," *Tappi*, 63:8, 86–88 (Aug. 1980).

* cited by examiner

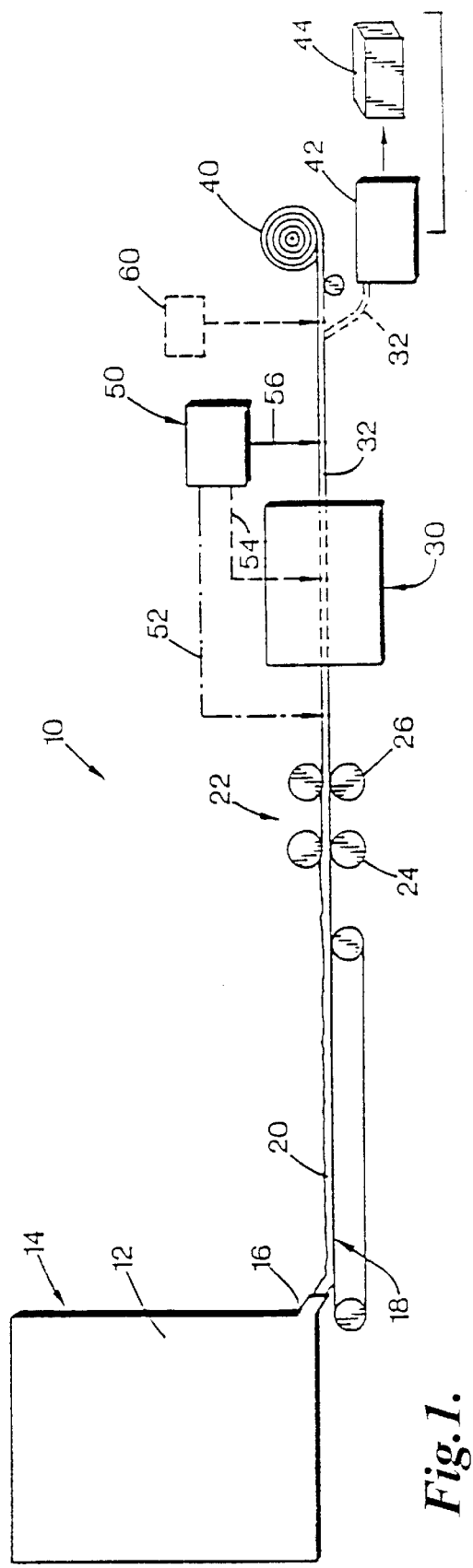
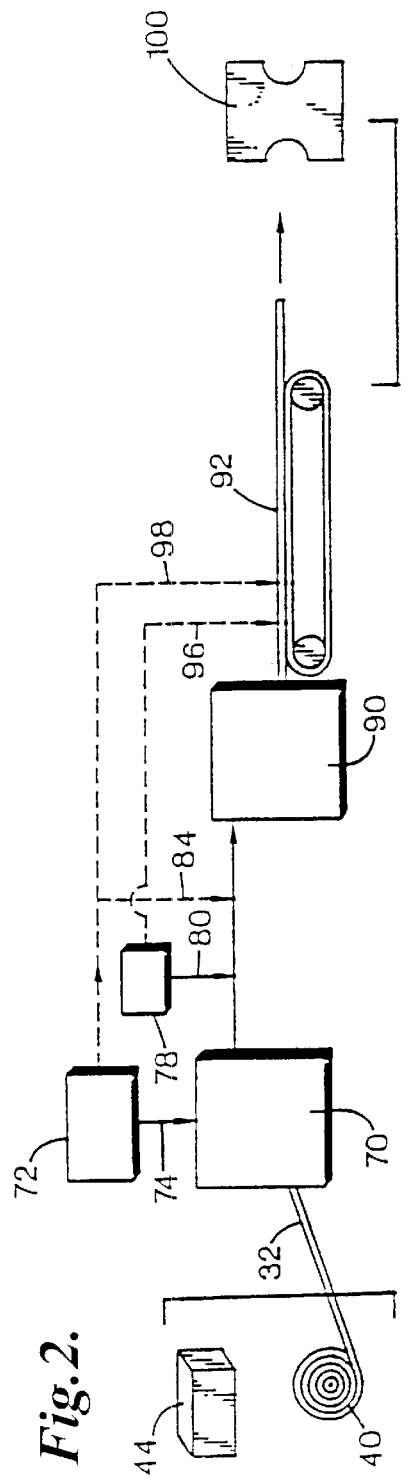
Fig.1.
Fig.2.

Fig. 6.
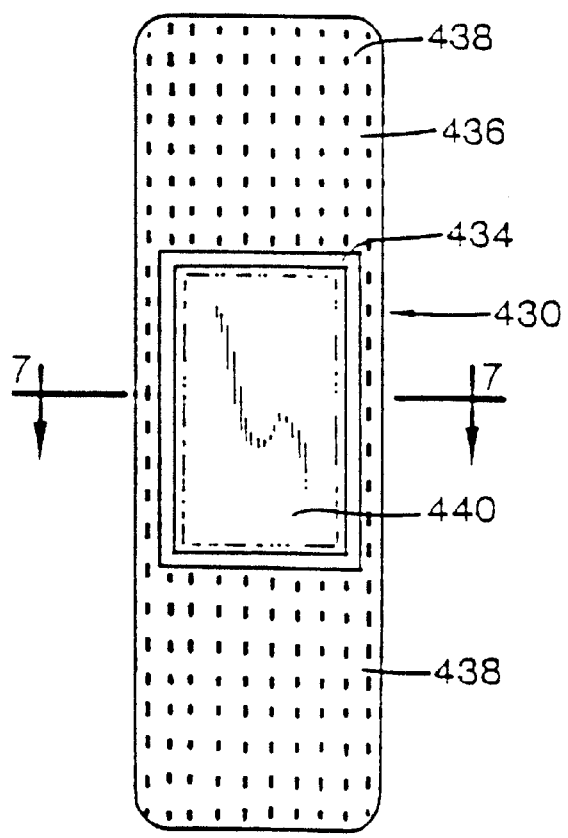
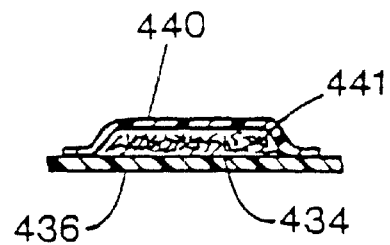
Fig. 7.

METHOD OF BINDING BINDER TREATED PARTICLES TO FIBERS

CROSS REFERENCE TO RELATED APPLICATIONS

This application is a continuation of prior application Ser. No. 08/791,335, filed Jan. 31, 1997, now U.S. Pat. No. 6,461,553, which in turn is a File Wrapper continuation of prior application Ser. No. 08/486,686 filed Jun. 7, 1995, now abandoned which in turn is a divisional of the prior application Ser. No. 08/108,218, filed Aug. 17, 1993, (now U.S. Pat. No. 5,641,561), which in turn is a CIP of the following prior application Ser. Nos. 07/931,059 (now U.S. Pat. No. 5,543,215); 07/931,277 (now U.S. Pat. No. 5,538,783); 07/931,213 (now U.S. Pat. No. 5,300,192); 07/931,278 (now U.S. Pat. No. 5,352,480); 07/931,284 (now U.S. Pat. No. 5,308,896); and 07/931,279 (now U.S. Pat. No. 5,589,256) each filed on Aug. 17, 1992, each of which is hereby incorporated in its entirety by reference.

FIELD OF THE INVENTION

This invention concerns polymeric and non-polymeric binders for particles and the use of such binders in binding particles to fibers. The fibers and bound particles may be easily densified by external application of pressure. The binders are reactivatable, and may be applied to particles, which thereafter may be bound to fibers on a wet-laid fiber sheet manufacturing line. In particular embodiments, the invention concerns binding superabsorbent particles to cellulosic fibers which may then be used, for example, to make absorbent fibers that are densified and incorporated into absorbent products. In other embodiments, the invention concerns the reactivation and use of binder coated particles, preferably at an article manufacturing plant, at a location remote from a pulp-sheet manufacturing line to bind superabsorbent and/or other particles to cellulosic fibers which may then be used, for example, as absorbent fibers incorporated into absorbent products.

BACKGROUND OF THE INVENTION

Superabsorbent polymers have been developed in recent years that are capable of absorbing many times their own weight of liquid. These polymers, which are also known as water insoluble hydrogels, have been used to increase the absorbency of sanitary products such as diapers and sanitary napkins. Superabsorbent polymers are often provided in the form of particulate powders, granules, or fibers that are distributed throughout absorbent cellulosic products to increase the absorbency of the product. Superabsorbent particles are described, for example, in U.S. Pat. Nos. 4,160,059; 4,676,784; 4,673,402; 5,002,814; and 5,057,166. Products such as diapers that incorporate absorbent hydrogels are shown in U.S. Patent Nos. 3,669,103 and 3,670,731.

One problem with the use of superabsorbents is that the superabsorbent material can be physically dislodged from the cellulosic fibers of an absorbent product. Separation of the superabsorbent from its substrate reduces the absorbency of the product and diminishes the effectiveness of the superabsorbent material. This problem was addressed in European Patent Application 442 185 A1, which discloses use of a polyaluminum chloride binder to bind an absorbent polymer to a fibrous substrate. The polyaluminum binder, however, suffers from the drawback of being an inorganic product that is not readily biodegradable. Moreover, that European patent does not offer any guidance for selecting binders other than polyaluminum chloride that would be useful in binding absorbent particles.

A method of immobilizing superabsorbents is disclosed in U.S. Pat. No. 4,410,571 in which a water swellable absorbent polymer is converted to a non-particulate immobilized confluent layer. Polymer particles are converted to a coated film by plasticizing them in a polyhydroxy organic compound such as glycerol, ethylene glycol, or propylene glycol. The superabsorbent assumes a non-particulate immobilized form that can be foamed onto a substrate. The individual particulate identity of the superabsorbent polymer is lost in this process. The confluent nature of the superabsorbent material can also result in gel blocking, in which absorption is diminished as the water swollen polymers block liquid passage through the film layer.

U.S. Patent Nos. 4,412,036 and 4,467,012 disclose absorbent laminates in which a hydrolyzed starch polyacrylonitrile graft copolymer and glycerol mixture is laminated between two tissue layers. The tissue layers are laminated to each other by applying external heat and pressure. The reaction conditions form covalent bonds between the tissue layers that firmly adhere the tissue layers to one another.

Numerous other patents have described methods of applying binders to fibrous webs. Examples include U.S. Pat. Nos. 2,757,150; 4,584,357; and 4,600,462. Such binders are not described as being useful in binding particulates, such as superabsorbent particles, to fibers. Yet other patents disclose crosslinking agents such as polycarboxylic acids that form covalent intrafiber bonds with individualized cellulose fibers, as in European Patent Application 440 472 A1; European Patent Application 427 317 A2; European Patent Application 427 316 A2; and European Patent Application 429 112 A2. The covalent intrafiber bonds are formed at elevated temperatures and increase the bulk of cellulose fibers treated with the crosslinker by forming intrafiber ester crosslinks. Crosslinking must occur under acidic conditions to prevent reversion of the ester bonds. The covalent bonds within the fibers produce a pulp sheet that is more difficult to compress to conventional pulp sheet densities than in an untreated sheet. Covalent crosslink bonds may also form between the fibers and particles, and occupy functional groups that would otherwise be available for absorption, hence absorption efficiency is decreased.

A particular disadvantage of forming covalent ester intrafiber crosslinks is that the resulting fiber product resists densification. Energy requirements for making densified absorbent products are increased because very high compression pressures must be used to densify the absorbent product. It would be advantageous to provide a method of enhancing densification of crosslinked fibers by reducing energy requirements for densification.

Many different types of particles other than superabsorbents may be added to fibers for different end uses. Antimicrobials, zeolites and fire retardants are but a few examples of particles that are added to fibers. It would be advantageous to provide a method of attaching particles that could be accommodated to the many different particle needs of end users. Moreover, it would be advantageous to reduce particulate waste in the attachment process, and simplify shipment of fiber products that require particulate addition. It would be further advantageous to bind particulates to fibers without requiring the shipment of bulk fibers with adhered particulates because shipping and excessive handling of these fibers subject them to mechanical impact which can dislodge some particles from the fibers. It would also be advantageous under some circumstances to incorporate binder coated particles onto fibers during the initial pulp sheet manufacturing process so that the fibers with particles are ready for use at a remote product manufacturing location. However, the particles are then subject to dislodgement during the subsequent manufacturing processes.

It has previously been important that particles added to cellulose products be insoluble in liquids such as water or liquid binders. It has been thought that liquid insolubility (particularly water insolubility) was an essential characteristic for particles bound to cellulose fibers because soluble particles would be dissolved by a water containing binder. Although the particle could eventually resolidify as the binder evaporated, dissolution of the particle in the binder would cause the particle to diffuse to areas of the product where it was not needed or desired. Water soluble particles have therefore not been used for particles that were to be bound to fibers using a binder.

SUMMARY OF THE INVENTION

The foregoing and other problems have been overcome by providing fibers with hydrogen bonding functional sites, and binders that have a volatility less than water. The binder has a functional group that forms a hydrogen bond with the fibers, and a functional group that is also capable of forming a hydrogen bond or a coordinate covalent bond with particles that have a hydrogen bonding or coordinate covalent bonding functionality. The binder is applied to the particles to at least partially coat the particles. The binder containing particles, when combined with the fibers, are bonded to the fibers by a bond that has been found to be resistant to mechanical disruption. A significant advantage of these binders is that the binder and particle together on the fiber have been found to reduce the pressure required to densify the fibers. This is particularly true for superabsorbent particles, and preferably comprises using superabsorbent particles and a binder in an active state. The binders can also be present on particles in an inactive state for more than a week, a month, or a even a year, then later activated or reactivated to bind particles to the fibers. Liquid binders (which includes neat liquids or aqueous solutions of solid binders) can be placed on the particles, dried, and later reactivated by moistening the particles. Alternatively, a dry solid binder may be blended with the particles and later activated by addition of a liquid. An inactive binder can also be activated by applying kinetic energy to the binder containing particles in the presence of the fibers. Typically, an inactive state is one where the binder and particles reach an equilibrium moisture content with the atmosphere (hereinafter referred to as "air dry"). Kinetic energy can be applied to the binder and fibers, for example and without limitation, by applying mechanical agitation, pressure from an external source, or using ultrasonics. In yet other embodiments, the binder may be activated or reactivated by heating the binder containing particles after applying the binder to the particles.

The capacity for activation or reactivation allows the binder to be applied to the particles, which are then shipped to distribution points with the binder in an inactive form. The binder is then activated at the distribution point (for example, a customer's facility) where binder containing particles are added to the fibers and bound thereto. As used herein, binder "activation" includes both activation of previously inactive binders (such as solid binders in the absence of liquid) or reactivation of previously active binders (such as a liquid binder that has been air dried). More typically, the particles are exposed to the binder, e.g. by spraying binder onto a stream of particles, as the particles are being deposited on a web of fibers or are otherwise being combined with the fibers. The binder binds the particles to the fibers. By applying binder primarily to the particles instead of directing the binder to the fibers, lesser quantities of binder are required to bind the particles to the fibers.

Another advantage of the present invention is that the binder containing particles can be applied to a fiber product in a pattern that corresponds to a desired distribution of particles in fibrous material. The binder may then be reactivated to bind the particles in place. A reactivation fluid, such as a reactivation liquid, for example, can be applied to binder containing particles deposited in the areas of a diaper that will be initially moistened by urine during use. Examples, without limitation, of suitable reactivation liquids include water, glycerin, lower alkyl alcohols, polyols, such as glycols, glycerin and monoglycerates, acetone, and combinations thereof, such as water and glycerin. When the reactivating fluid is a liquid, for example water, the liquid may be sprayed or otherwise applied and may be provided in the form of a gas. When water is the reactivating liquid, then it may be provided as steam or moisture-laden gas, such as humid air. Other liquid reactivation fluids may be applied in the same manner. Binder containing particles, such as superabsorbent particles can be added to areas of the diaper to which an activation fluid is or will be applied and will be adhered almost exclusively in those areas where initial urine absorption is required. Targeted activation of binder containing particles allows the particles to be efficiently and economically attached to the fibers, with reduced particle wastage. Moreover, targeted binder activation and particle adherence increases the absorptive efficiency of the product by diminishing excessive wicking of liquid within the plane of an absorptive product.

The particles of the present invention may be bound to the fibers with a polymeric or non-polymeric binder. The binder comprises binder molecules wherein the binder molecules have at least one functional group capable of forming a hydrogen bond or coordinate covalent bond with the particles and at least one functional group capable of forming a hydrogen bond with fibrous material. The polymeric binder may be selected from the group consisting of polyglycols, especially polyethylene glycol or poly (propyleneglycol), a polycarboxylic acid, a polycarboxylate, a poly(lactone) polyol, such as diols, a polyamide, a polyamine, a polysulfonic acid, a polysulfonate and combinations thereof. Specific examples of some of these binders, without limitation, are as follows: polyglycols include polypropylene glycol (PPG) and polyethylene glycol (PEG); poly(lactone) polyols include poly(caprolactone) diol; polycarboxylic acids include polyacrylic acid (PAA); polyamides include polyacrylamide or polypeptides; polyamines include polyethylenimine and polyvinylpyridine; polysulfonic acids or polysulfonates include poly(sodium-4-styrenesulfonate) or poly(2-acrylamido-methyl-1-propanesulfonic acid); and copolymers thereof (for example a polypropylene glycol/polyethylene glycol copolymer). The polymeric binder typically has repeating units. The repeating unit may be the backbone of a compound, such as with a polypeptide, wherein the repeating polyamides occur in the peptide chain. The repeating unit may also refer to units other than backbones, for instance a repeating acrylic acid unit. In such a case, the repeating units may be the same or different. The binder has a functional group capable of forming a hydrogen bond or a coordinate covalent bond with particles, and a functional group capable of forming a hydrogen bond with the fibers. At this time, the most preferred polymeric binder is polyethylene glycol although another especially preferred polymeric binder is an amide binder such as a polypeptide binder with polyglycine being a specifically preferred example.

The non-polymeric binder has a volatility less than water, a functional group that is capable of forming a hydrogen bond or coordinate covalent bond with the particles, and a functional group that is capable of forming a hydrogen bond with the cellulose or other fibers. The non-polymeric binder is an organic binder, and preferably includes a functional group selected from the group consisting of a carboxyl (for example, carboxylic acids), a carboxylate, a carbonyl (for example, aldehydes), a sulfonic acid, a sulfonate, a phosphoric acid, a phosphate, an amide, an amine, a hydroxyl (such as an alcohol) and combinations thereof (for example, an amino acid or an hydroxy acid), wherein there are at least two functionalities on the molecule selected from this group, and the two functionalities are the same or different. Examples of such binders include polyols, polyamines (a non-polymeric organic binder with more than one amine group), polyamides (a non-polymeric organic binder with more than one amide group), polycarboxylic acids (a non-polymeric organic binder with more than one carboxylic acid functionality), polyaldehydes (a non-polymeric organic binder with more than one aldehyde), amino alcohols, hydroxy acids and other binders. These binders have functional groups that are capable of forming the specified bonds with the particles and fibers.

More preferably, the organic non-polymeric binder is selected from the group consisting of glycerin, a glyceride monoester, including monoglycerides, a glycerin diester, including diglycerides, glyoxal, ascorbic acid, urea, glycine, pentaerythritol, a monosaccharide or a disaccharide, citric acid, tartaric acid, taurine (2-aminoethanesulfonic acid), p-aminosalicylic acid, dipropylene glycol, urea derivatives such as DMDHEU, and combinations thereof. Suitable saccharides include glucose, sucrose, lactose, ribose, fructose, mannose, arabinose, and erythrose. The preferred binders are non-polymeric molecules with a plurality of hydrogen bonding functionalities that permit the binder to form hydrogen bonds to both the fibers and particles. Particularly preferred binders include those that can form five or six membered rings, most preferably six membered rings, with a functional group on the particle surface. At present, glycerin, a glycerin monoester, a glycerin diester, and blends of these with urea are the preferred binders. At this time, a specifically preferred non-polymeric binder is glycerin.

The fibrous material may be cellulosic or synthetic fibers that are capable of forming hydrogen bonds with the binder, while the particles are selected to be of the type that are capable of forming hydrogen bonds or coordinate covalent bonds with the binder. It has unexpectedly been found that this binder system secures particles to fibers exceptionally well. A superior fibrous product is therefore produced that has improved absorbent properties as compared to unbound or covalently bound particles. Formation of the noncovalent bond allows production of a fiber product that is easily manufactured and a web that is easily densified, and that is readily biodegradable and disposable.

In one preferred embodiment, an absorbent product comprises a fibrous cellulosic mat that contains superabsorbent hydrogel particles in particulate form. The superabsorbent particles are capable of forming hydrogen bonds or coordinate covalent bonds with the binder, depending upon the binder, while the binder in turn is capable of forming hydrogen bonds with the hydroxyl groups of the cellulose fibers. These noncovalent, relatively flexible bonds between the binder and particles maintain the particles in contact with the fibers, and resist dislodgement of the particles by mechanical forces applied to the mat during manufacture, storage or use. The amount of binder present typically depends on a number of factors, including the nature of the binder and particles, and whether the particles are immediately added to the fibers or after a period of time. Hence, one skilled in the art will realize that the amount of binder suitable and particularly useful for a particular application will vary. However, the binder may suitably be present in an amount of from about 0.01 to 50 percent of the total weight of the particles, preferably from 0.03 to 20 percent, more preferably 0.03 to 5 percent and most preferably 0.03 to 1 percent. This lower percentage range produces very strong bonds that would require a much higher quantity of binder if the binder were applied to the fibers instead of the particles. The particles bound by the binder of the present invention (via hydrogen/coordinate covalent bonds) may suitably be present in an amount of 0.05 to 80 percent of the total weight of the fibrous material and the particles, preferably 1 to 80 percent or 5 to 80 percent, or more than 5 percent by weight. A particularly suitable range of particles is 5 to 70 percent by weight of the fibrous material and particles. A preferred weight ratio of particle to binder is 90:1 to 500:1. An example of a suitable particle is a superabsorbent polymer such as a starch graft polyacrylate hydrogel fine or larger size particle such as a granule, which is capable of forming hydrogen bonds with the binder. The binder also is capable of forming hydrogen bonds with the hydroxyl groups of the cellulose, thereby securely attaching the superabsorbent particles to the fibers.

The present invention also includes a method of binding particles to fibers wherein the particles are insoluble in the binder (and soluble in water) and therefore retain their solid particulate form following binding. The particles, whether water soluble or not, preferably have functional groups that can form hydrogen bonds or coordinate covalent bonds with the binder, and the binder in turn is capable of forming hydrogen bonds to the fibers. Other particles without the desired functionality may also be included in the fiber product, but such particles will not be bound as strongly in the same manner.

In especially preferred embodiments, the fibers are cellulosic and the particles are superabsorbent particles that are bound to the binder by hydrogen bonds. The fibers also may be continuous or discontinuous synthetic or natural fibers having a hydrogen bonding functional group that hydrogen bonds with the binder. The binder is suitably applied to the particles in an amount of at least 0.03 percent, and preferably no more than 80 percent, more preferably no more than 20 percent and most preferably 0.1 to 3 percent, by total weight of the particles. The particles may be bound to the fibers at less than 150° C. or without any external application of heat at ambient temperature (e.g., about 25° C.). Particles may also be bound in the absence of any external application of pressure, or in the absence of external heat and pressure.

In some embodiments the binder is associated with the particles as a solid (for example, a dry powder or a dried liquid), and the fibers contain at least 7 percent water by weight when the binding step is performed. This level of moisture in the fibers provides sufficient mobility of reactants to allow the particles and fibers to bind well to each other. When a liquid binder is used (for example, glycerin or a solution of glycine powder), the fibers suitably contain at least about 0.5 percent water by weight. A solid binder is suitably used with fibers having less than 0.5 percent water by weight if the binder is heated above its melting point to liquefy it. A solid binder may be thermoplastic or meltable, such that it can be heated above its melting point and then cooled to fuse fibers to each other. The thermoplastic properties of the binder can also provide additional mechanical adherence between the particles and fibers. In some embodiments, a meltable binder such as urea may be employed which can adhere particles both physically and with hydrogen bonding.

In other embodiments, the particles are soluble in water but have reduced solubility in the binder such that the particles can be bound in solid particulate form to the fibers. Addition of the binder does not dissolve the particle and cause it to diffuse away from its desired site of attachment to the fibers.

The invention also is directed to fibrous products produced by any of the methods described herein and to absorbent products or articles comprised of such fibrous products.

The present invention relates to the above objects, features and advantages individually as well as collectively. The foregoing and other features and advantages of the invention will become more apparent from the following detailed descriptions and accompanying drawings.

BRIEF DESCRIPTION OF THE DRAWINGS

FIG. 1 is a schematic illustration of a wet laid sheet manufacturing line illustrating the application of binder coated particles in accordance with the present invention during the manufacture of a fiber sheet.

FIG. 2 is a schematic illustration of a web manufacturing line illustrating binder reactivation and particulate attachment process in accordance with the present invention.

FIG. 6 illustrates a plan view of a bandage incorporating particles with binder adhered to fibers in accordance with the present invention.

FIG. 7 is a sectional view of the bandage of FIG. 6, taken along line 7—7 of FIG. 6.

DETAILED DESCRIPTION OF SEVERAL PREFERRED EMBODIMENTS OF THE INVENTION

I. Processing of Fibers

Figure 3:
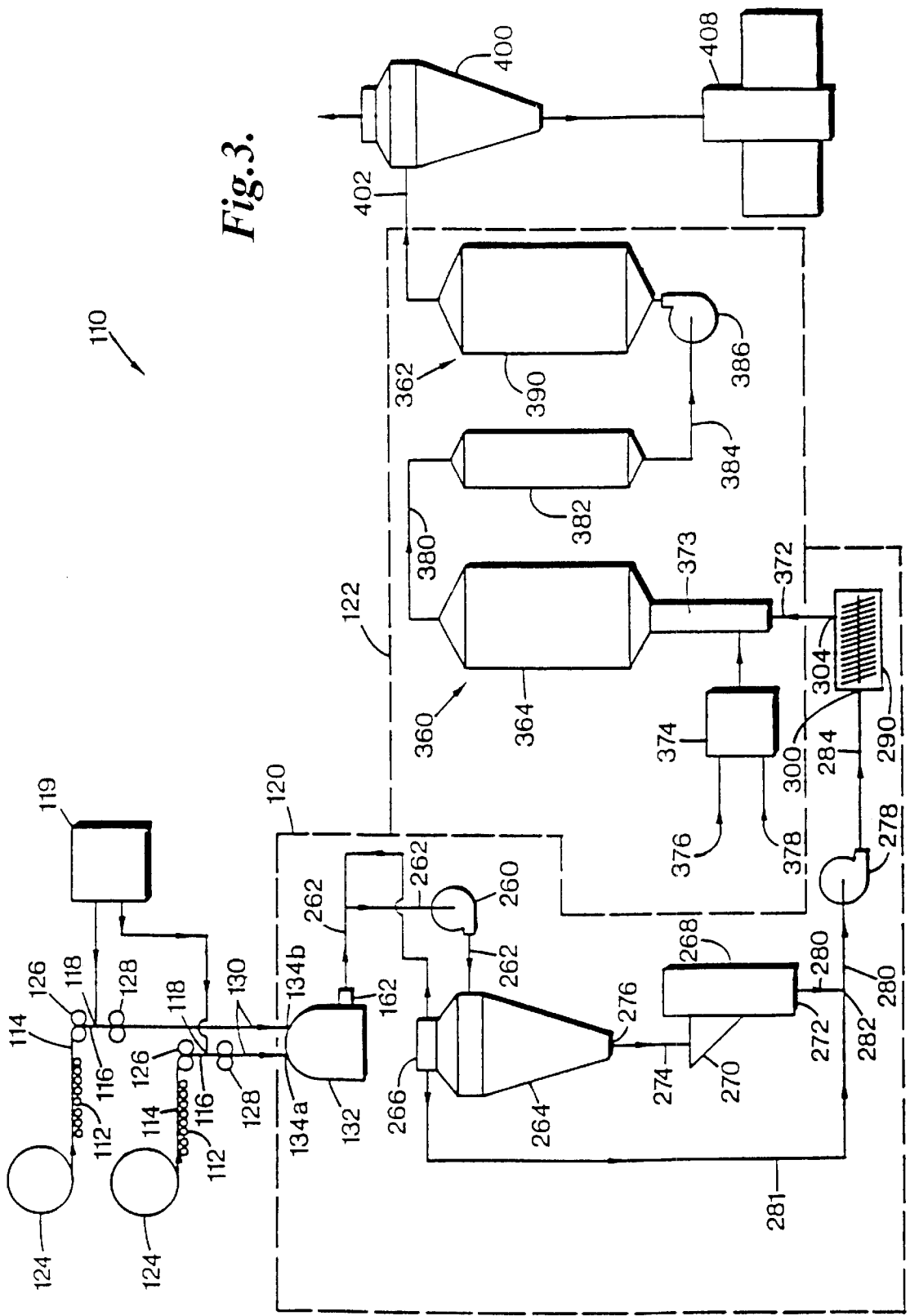
FIG. 3 is a schematic depiction of the components of an apparatus of the present invention that produce high bulk fibers.

FIG. 1 illustrates a wet laid sheet manufacturing line such as a pulp sheet manufacturing line 10. In this manufacturing line, a pulp slurry 12 is delivered from a headbox 14 through a slice 16 and onto a Fourdrinier wire 18. The pulp slurry 12 typically includes cellulose fibers such as wood pulp fibers and may also include synthetic or other non-cellulose fibers as part of the slurry. Water is drawn from the pulp deposited on wire 18 by a conventional vacuum system, not shown, leaving a deposited pulp sheet 20 which is carried through a dewatering station 22, illustrated in this case as two sets of calendar rolls 24, 26 each defining a respective nip through which the pulp sheet or mat 20 passes. From the dewatering station, the pulp sheet 20 enters a drying section 30 of the pulp manufacturing line. In a conventional pulp sheet manufacturing line, drying section 30 may include multiple canister dryers with the pulp mat 20 following a serpentine path around the respective canister dryers and emerging as a dried sheet or mat 32 from the outlet of the drying section 30. Other alternate drying mechanisms, alone or in addition to canister dryers, may be included in the drying stage 30. The dried pulp sheet 32 has a maximum moisture content pursuant to the manufacturer's specifications. Typically, the maximum moisture content is no more than 10% by weight of the fibers and most preferably no more than about 6% to 8% by weight. Otherwise, the fibers tend to be too damp. Unless overly damp fibers are immediately used, these fibers are subject to degradation by, for example, mold or the like. The dried sheet 32 is taken up on a roll 40 for transportation to a remote location, that is, one separate from the pulp sheet manufacturing line, such as at a user's plant for use in manufacturing products. Alternatively, the dried sheet 32 is collected in a baling apparatus 42 from which bales of the pulp 44 are obtained for transport to a remote location.

A binder of the type explained in detail below is applied to particles and then the binder containing particles are applied to the pulp sheet from one or more particle applying devices, one of which is indicated at 50 in FIG. 1. Any binder applying device may be used for applying binder to particles, such as sprayers, or immersion applicators or the like. Sprayers are typically easier to utilize and incorporate into a pulp sheet manufacturing line. The binder is applied to the particles and then the particles are deposited onto the pulp sheet where the binder adheres the particles to the fibers of the sheet. The binder also may be sprayed or otherwise applied to the particles as they fall or are otherwise deposited onto the sheet. Also, the binder may be combined with the particles at another location, allowed to dry or become inactive, and then applied to the sheet. The binder may then be activated as explained below. Also, the moisture in the sheet may be enough to activate the binder for binding particles to the fibers. As indicated by the arrows 52, 54 and 56, the binder containing particles may be applied at various locations or at multiple locations on the pulp sheet manufacturing line, such as ahead of the drying stage 30 (indicated by line 52), intermediate the drying stage 30 (as indicated by line 54), or downstream from the drying stage 30 (as indicated by the line 56). Particles with water-soluble binders, such as non-polymeric urea, are typically applied at a location where sufficient drying can still take place in the drying stage to produce a dried binder particle containing fiber sheet with no more than the maximum desired moisture content. Consequently, to take advantage of the drying stage 30, particles with wet water-based binders may be applied at locations 52 or 54. If wet water-based binder containing particles are applied at location 56 in an amount which would cause the moisture content of the sheet to exceed the desired maximum level, an additional drying stage (not shown) may be included in the pulp manufacturing line to bring the moisture content down to the desired level.

Particles with a non-aqueous based binder, such as glycerin, would most preferably be added downstream from the drying stage at location 56 or during the drying stage as indicated by location 54. However, particles with liquid non-aqueous binders may also be added at a location, such as location 52, upstream of the drying stage. At this latter location, the water in the wet web at this point may tend to attract these binders into the mat or sheet as many of the binders tend to be hydroscopic. Since non-aqueous binders typically do not enhance the degradation of the product due to the addition of moisture to the sheet, particles with such binders can be applied downstream from the drying stage without bringing the moisture content of the sheet above the desired maximum level.

Again, the binder containing particulate materials, selected as explained below, may be added to the sheet and adhered thereto by the binders on the pulp manufacturing line. Another suitable particulate applicator is indicated at 60 and may comprise a bulk or volumetric metering device. These particles may be sprinkled, poured or otherwise added to the sheet. To facilitate the adherence of these particulates to the sheet at this location, enough moisture must remain in the sheet or on the particles, in the case of aqueous binders on the particles, to enable the bonding between the particles and fibers as explained below. For non-aqueous binders, the particles in this case are preferably added while the binder is still wet or heated to facilitate the binding.

Although the above approach is advantageous because the particles are strongly bound to the fibers, during transportation of rolls or bales of these fibers it is possible for particles to become dislodged by mechanical impact during transport. In addition, this approach interferes with the customization of the fiber application at a user's location. For example, a user may want the capability of selecting particular types or brands of particles for adherence to the fibers in the user's products, without having this selection made by a pulp-sheet manufacturer who incorporates the particles into the pulp sheet during its manufacture. Also, certain particles may degrade over time, making it advantageous to add such particles immediately prior to incorporation into products. For example, superabsorbent particles are susceptible to absorbing moisture from the atmosphere during shipment. Particles with a relatively short shelf life, such as certain zeolites (e.g. Abscents with odor absorbing materials which can become saturated with odors over time) being one example, may also degrade over time. Another example is zeolites with silver salts as antimicrobial agents which can photodegrade. Therefore, it is also advantageous to provide a fibrous product in which the end user of the product may incorporate the desired particles with binders at the time the fibers are converted into products.

Therefore, in keeping with this latter preferred approach, as illustrated in FIG. 2, the respective rolls 40 or bales 44 of fibers, without particles, are transported to a remote location for use by a user. These rolls or bales (or otherwise transported fibers, e.g., bagged, containerized or otherwise in bulk form) are then refiberized by a fiberizing apparatus 70. Although any fiberizer may be used, a typical fiberizing apparatus 70 is a hammermill which may be used alone or in conjunction with other devices such as picker rolls or the like for breaking up the sheet 32 or bales 42 into individual fibers.

A particulate material adding mechanism 72 (e.g., like mechanism 60) delivers the desired binder coated particulate materials to the fibers at the desired location in the user's process. Again, the device 72 typically comprises a metering mechanism, although any suitable device for adding particulates to fibrous materials may be used. For example, the particulates may be delivered as indicated by line 74 to the fiberizing apparatus 70. In the case of some binders, agitation of fibers within the fiberizer 70, as explained in greater detail below, reactivates the binders and causes the particulates to be adhered to the fibers by the binder. Alternatively, a reactivating fluid, which may be a liquid such as, for example, water, glycerin, lower-alkyl alcohols, polyols, acetone, and combinations thereof, such as water and glycerin, may be sprayed or otherwise applied to the fibers, such as from a reactivation fluid tank or source 78 by way of a sprayer (not shown) at location 80. The particles may then be applied, as indicated by line 84 to the fibers downstream from the application of the reactivation liquid 80. The binder on the particles may be reactivated by the activating fluid to adhere to the fibers. Alternatively, the binder containing particles may be added prior to or at location 80 where they are adhered to the fibers by the binder upon reactivation of the binder at location 80. Binder may also be combined with the particles as the particles are added to the fiber sheet. As yet another alternative, the fiberized fibers are delivered to an air-laying device 90 and reformed into a desired product such as a web indicated at 92. In the case of air-laid fibers, the reactivation fluid or liquid may be applied to the web at location 96 with the binder containing particles when being added at location 98 as shown with the reactivated binder then adhering the particles to the fibers. The particles with binder may be applied at a location in the process upstream from the application of the reactivating liquid at location 96. Alternatively, the activating fluid may be added simultaneously with the addition of binder coated particles, so that the reactivation occurs simultaneously with the addition of particles. The reactivating fluid also may be added after the binder coated particles are added to the fibers. In addition, the binder coated particles may be applied to specifically defined locations on the web 92, such as in target zones of an absorbent core of a product, thereby minimizing the wasting of the particulate material. A specific example of a target zone is the crotch region of a diaper where most diaper wetting would occur. The application of superabsorbent particles to such a zone places these particles at a location where they are most useful in absorbing liquid. The web 92, with or without other components of the end user's product, is then processed into the user's product, such as being included within a disposable diaper 100.

Again, with this approach, the end user of the fibers may readily select particles to be applied to its product and may, if required, activate the binder as required to enhance the efficient production of the user's product. In addition, the user has flexibility in air laying fibers with binder-coated particles or otherwise combining the binder coated particles into a finished product with the desired particulates. Not only is handling and shipping of the particulate-containing products avoided by the manufacturer of the pulp sheet, enhanced adhesion of particulates to the fibers results because the particles are not subjected to mechanical forces between the location of manufacture of the fibers and the location at which the particulate materials and binder are added.

II. Fiber Characteristics

The present invention includes a method of binding particles to fibers, and the product, including absorbent end-products, that are produced by such method. In particularly preferred embodiments, the product is a cellulosic or synthetic fiber to which superabsorbent hydrogel polymer particles are adhered by a binder, and absorbent products made therefrom. The invention also includes a combination of wood pulp and certain binders, which for the purpose of this combination are bulk fibers in roll form having a basis weight of at least 350 grams per square meter (g/m$^2$) or bale form. The bulk fibers can have a density of at least about 400 kg/m$^3$. Preferred bulk fibers are wood pulp fibers or softwood pulp fibers. The pulp fibers may be chemical or thermomechanical or chemithermomechanical or combinations thereof. The preferred pulp fiber is chemical. Suitable fibers include wood-pulp fibers, which can be obtained from well known chemical processes such as the kraft and sulfite processes. In these processes, the best starting material is prepared from long fiber coniferous wood species, such as pine, douglas fir, spruce and hemlock. Wood pulp fibers can also be obtained from mechanical processes, such as ground wood, mechanical, thermomechanical, chemimechanical, and chemithermomechanical pulp processes. The fibers are preferably elongated, for example having a length to width ratio of about 10:1 to 5:1.

The fibers of the present invention also include fibers that are pretreated prior to the application of a binder to the fibers. This pretreatment may include physical treatment, such as subjecting the fibers to steam or chemical treatment, such as cross-linking the fibers. Although not to be construed as a limitation, examples of pretreating fibers include the application of fire retardants to the fibers, such as by spraying the fibers with fire retardant chemicals. Specific fire-retardant chemicals include, by way of example, sodium borate/boric acid, urea, urea/phosphates, etc. In addition, the fibers may be pretreated with surfactants or other liquids, such as water or solvents, which modify the surface of the fibers. Other pretreatments include exposure to antimicrobials or pigments.

The fibers also may be pretreated in a way which increases their wettability. The fibers also may be pretreated with conventional cross-linking materials and may be twisted or crimped, as desired. Pretreating cellulose fibers with chemicals which result in lignin or cellulose rich fiber surfaces also may be performed in a conventional manner.

Bleaching processes, such as chlorine or ozone/oxygen bleaching may also be used in pretreating the fibers. In addition, the fibers may be pretreated, as by slurrying the fibers in baths containing various solutions. For example, antimicrobial solutions (such as solutions of antimicrobial particles as set forth below), as well as solutions of fertilizers and pesticides, and/or fragrances and flavors, for release over time during the life of the fibers. Fibers pretreated with other chemicals, such as thermoplastic and thermoset resins also may be used. Combinations of pretreatments also may be employed with the resulting pretreated fibers then being subjected to the application of the binder coating as explained below.

Ground wood fibers, recycled or secondary wood-pulp fibers, and bleached and unbleached wood-pulp fibers can be used. Details of the production of wood pulp fibers are well known to those skilled in the art. These fibers are commercially available from a number of companies, including Weyerhaeuser Company, the assignee of the present invention.

The fibers also can be any of a variety of other natural or synthetic fibers; however, all of the fibers to which particles are attached in accordance with the present invention include a hydrogen-bonding functionality. This does not preclude the blending of such fibers with fibers lacking this characteristic. However, the fibers lacking a hydrogen bonding functionality will not have particles bonded thereto with the strength and manner of the bonds that would be present if the fibers had a hydrogen-bonding functionality.

A hydrogen bond is an intermolecular force that occurs between hydrogen atoms that are covalently bonded to small, strongly electronegative elements (such as nitrogen and oxygen) and nonbonding electron pairs on other such electronegative elements. A hydrogen bonding functionality is a functional group that contains an oxygen or nitrogen atom, for example hydroxyls, carboxyls, sulfonic acids, sulfonamides, ethers., esters, epoxides, carbonyls, amines, urethanes and others, that is capable of forming a hydrogen bond. The orbitals of the nonbonding electron pairs on the oxygen or nitrogen overlap with the relatively empty 1s orbital of the hydrogen covalently bonded to another nitrogen or oxygen atom. The 1s orbital of the hydrogen is relatively empty due to the unequal sharing of the electrons in the covalent bond between it and the small electronegative atom (oxygen or nitrogen) to which it is bound.

Specific examples of natural fibers that contain a hydrogen bonding functionality include chopped silk fibers, wood pulp fibers, bagasse, hemp, jute, rice, wheat, bamboo, corn, sisal, cotton, flax, kenaf, peat moss, and mixtures thereof. Suitable synthetic fibers with hydrogen bonding functionalities include acrylic, polyester, carboxylated polyolefins, rayon and nylon. The hydrogen-bonding functionality is an ester in acrylic fibers and a carboxylic acid in carboxylated polyolefin fibers, an ester in polyester, an amide in nylon, and a hydroxyl in rayon. Polyethylene and polypropylene would be unsuitable fibers for use in particle to fiber bonding in the manner of the present invention because they include only carbons and hydrogens without any other atoms, such as oxygens or nitrogens, that can participate in hydrogen bonds.

For purposes of convenience, and not to be construed as a limitation, the following description proceeds with reference to the treatment of individual chemical wood-pulp fibers. The fibers are individualized, for example by defiberization in a hammermill. Such individualized fibers are conventionally formed into a mat, and are commercially available, for example as NB 416 fibers from the Weyerhaeuser company. Another suitable cellulosic mat would include Rayfloc JLD from ITT Rayonier. The cellulose fibers may be in the form of a cellulosic web or loose cellulose fibers.

III. Particle Characteristics

In accordance with the present invention, particles are added to the fibers to give the fibers desired properties, such as, by way of example only, increased absorbency, abrasiveness, or antimicrobial activity. The particle can be any particulate material that has the desired property and which is capable of forming hydrogen bonds or coordinate covalent bonds with the binder. It should be understood that some portion of the particles may dissolve in the binder form. In certain cases, the particles may be substantially soluble in both water and binder.

Hydrogen bonds can be formed, as discussed above, by particles that contain certain functional groups, particularly those having an oxygen or nitrogen. Coordinate covalent bonds, in contrast, are formed by donation of a lone pair of electrons on one atom to an empty orbital of another atom. Coordinate covalent bonds differ from covalent bonds in that covalent bonds are formed by a pair of electrons wherein one of the electrons is donated from each of the atoms that participate in the bond. Particles can form coordinate covalent bonds if they have an empty p or d or f orbital that is capable of accepting a pair of electrons from the binder.

A coordinate covalent bond occurs between a donor atom that has a lone pair of electrons to donate to the bond, and an acceptor atom that has an empty orbital to accept the lone pair of electrons from the donor. According to the Aufbau and Pauli principles, electrons occupy the lobes of atomic orbitals one at a time with a maximum of two electrons (with opposite spins) per lobe. The most basic orbital is the s orbital, which is available for bonding the elements in the first row of the periodic table. In the second row of the periodic table, electrons fill first the 2s orbital of Li and Be. However, metals in periods less than three do not have sufficient affinity for electrons to participate in coordinate covalent bonding. Beginning with Group IIIB (boron), the three p orbitals participate in coordinate covalent bonding and the lobes of the p orbitals begin to fill. Boron has one electron in one of the 2p orbitals, thus leaving the other 2 p orbitals empty and available for coordinate covalent bonding. An example of a coordinate covalently bonded boron containing particle is boric acid, which is used as an astringent, antiseptic and fire retardant. As shown below, the boron atom of boric acid acts as an acceptor for a lone pair of electrons donated by an oxygen atom of polypropylene glycol (PPG), thereby forming a coordinate covalent bond between a boric acid particle and a PPG binder. The depiction of boric acid shown below may not be typical of the aqueous chemistry of boron, but rather is provided to illustrate the type of bonding that is believed to occur in a coordinate covalent bond.

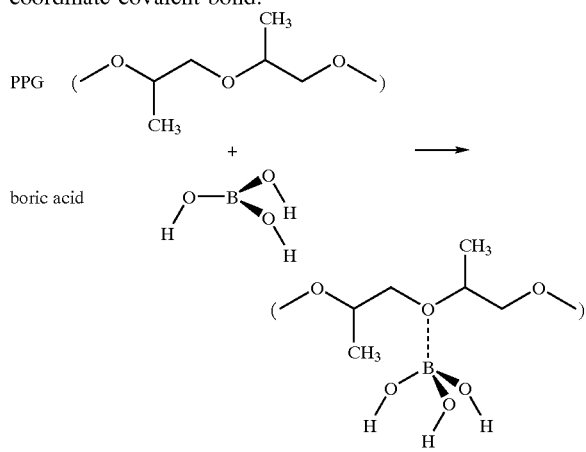

The next element, carbon, usually hybridizes to have one electron in the 2s orbital and the three remaining electrons are singly placed in the three p orbitals. This leaves no lobes empty for coordinate covalent bonding and electron additions proceeding further across that row of the periodic table also leave no lobes empty. Hence, boron is the only element in the second row of the periodic table that is capable of forming coordinate covalent bonds.

Next the third row begins to fill, and the two 3s electrons fill first in sodium and magnesium, but these metals in groups Ia and IIa do not form coordinate covalent bonds as discussed above. Then aluminum, like boron, places one electron in one of the 3p lobes, and the two other 3p lobes are empty and available for coordinate covalent bonding. The same trends continue across the third row, but the third row elements also have available five 3d lobes so the potential for coordination bonding exists even though 3p orbitals are occupied in the third row. Hence, Al, P, S, and Cl are capable of accepting a pair of electrons from an electron-pair donor to form a coordinate covalent bond. An example of this is found in the bonding in $PCl_5$, aluminum trihydrate, or phosphorous pentasulfide. A phosphorous pentasulfide particle can be used to increase flammability of a product, while aluminum trihydrate is a fire retardant. An example of a coordinate covalently bonded aluminum compound is

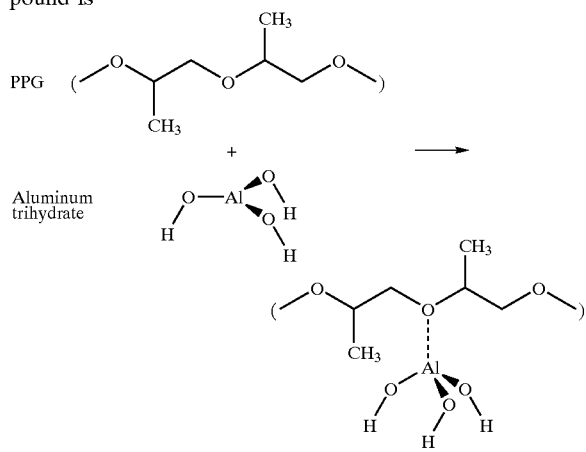

aluminum trihydrate, which may participate in a coordinate covalent bond with a polypropylene glycol (PPG) polymer.

In this example, the aluminum atom of aluminum trihydrate acts as an electron acceptor for an electron pair donated by an oxygen atom of the polypropylene glycol (PPG) binder. The depiction of aluminum trihydrate shown above may not be typical of the aqueous chemistry of aluminum, but rather is provided to illustrate the type of bonding that may occur in a coordinate covalent bond.

In the next row, the 4s orbital is filled first, then the 3d lobes begin to fill one electron per lobe until all have added a single then a second electron to each lobe until all lobes are filled. However, 4p and 4f orbitals also are available, hence many of the. transition elements are capable of forming coordinate covalent bonds.

The elements that have empty orbitals that participate in coordinate covalent bonding include all those except the metals (which excludes hydrogen) in periods one and two, and C, N, O, F, Ne and He. The metals do not have sufficient affinity for electrons to participate in coordinate covalent bonding. Especially preferred particles contain boron, aluminum, iron, rhodium, osmium, platinum, and palladium, and most particularly boron. Examples of particles that are capable of coordinate covalent bonding are aluminum trihydrate, antimony oxide, arsenic disulfide, bismuth aluminate, bismuth iodide oxide, bismuth phosphate, bismuth subcarbonate, bismuth subgallate, cadmium salycilate, chromic carbonate, chromic hydroxide, chromic oxide, and chromic phosphate. All of the polymeric binders of the present invention [polyglycols (such as PPG), polycarboxylic acids (such as PAA), poly(lactone) polyols (such as poly(caprolactone) diol), polyamides, polyamines, etc.] are capable of donating a lone pair of electrons from an electronegative atom, such as oxygen or nitrogen, to form a coordinate covalent bond with a suitable particle that includes an atom having an empty orbital for accepting electrons to form a coordinate covalent bond.

IV. Superabsorbent Particles

In one disclosed embodiment the added particles are superabsorbent particles, which comprise polymers that swell on exposure to water and form a hydrated gel (hydrogel) by absorbing large amounts of water. Superabsorbents are defined herein as materials that exhibit the ability to absorb large quantities of liquid, i.e., in excess of 10 to 15 parts of liquid per part thereof. These superabsorbent materials generally fall into three classes, namely starch graft copolymers, crosslinked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a crosslinked polyacrylate salt, carboxylated cellulose, and a neutralized crosslinked isobutylene-maleic anhydride copolymer.

Superabsorbent particles are available commercially, for example starch graft polyacrylate hydrogel fines (IM 1000F) from Hoechst-Celanese of Portsmouth, Va., or larger particles such as granules. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), FAVOR (supplied by Stockhausen of Greensboro, N.C., and NORSOCRYL (supplied by Atochem). The superabsorbent particles come in a variety of sizes and morphologies, for example IM 1000 and IM 1000F. The 1000F is finer and will pass through a 200 mesh screen whereas IM 1000 has some particles that will not pass through a 60 mesh screen. Another type of superabsorbent particle is IM 5600 (agglomerated fines). Superabsorbent particulate hydrophilic polymers also are described in detail in U.S. Pat. No. 4,102,340. That patent discloses hydrocolloid absorbent materials such as cross-linked polyacrylamides.

V. Other Particles

Many particles that form hydrogen bonds or coordinate covalent bonds are suitable for use with the present invention. Some such particles are listed in Table I with an indication of the function of the listed particles. The particles listed in Table I are water-insoluble particles.

TABLE I

Water-Insoluble Particulates For Binding

| Name | Function |
|---|---|
| Aluminum Trihydrate | Fire retardant, astringent |
| Acediasulfone | Antibacterial |
| Agaricic acid | Antiperspirant |
| Alclometastone | Topical anti-inflammatory |
| Calcium alginate | Topical hemostatic |
| Amidomycin | Fungicide |
| Antimony oxide | Fire retardant |
| Apigenin | Yellow dye, mordant |
| Arsenic disulfide | Red Pigment |
| Aspirin | Anti-inflammatory; antipyretic |
| Azanidazole | Antiprotozoal (Trichomonas) |
| Azelaic acid | Antiacne |
| Baicalein | Astringent |
| Bendazac | Anti-inflammatory |
| Benomyl | Fungicide; ascaricide |
| Benzestrol | Estrogen |
| Benzylpenicillinic acid | Antibacterial |
| Benzylsulfamide | Antibacterial |
| Bergaptene | Antipsoriatic |
| Betasine | Iodine source |
| Bezitramide | Narcotic analgesic |
| Bibrocathol | Topical antiseptic |
| Bietanautine | Antihistaminic |
| Bifenox | Herbicide |
| Bifonazole | Antifungal |
| Binapacryl | Fungicide, miticide |
| Bis(p-chlorophenoxy)methane | Miticide |
| Bismuth aluminate | Antacid |
| Bismuth iodide oxide | Anti-infective |
| Bismuth phosphate | Antacid; protectant |
| Bismuth subcarbonate | Topical protectant |
| Bismuth subgallate | Astringent, antacid; protectant |
| Bisphenol A | Fungicide |
| Bitertanol | Agricultural fungicide |
| Bithionol | Topical anti-infective |
| Bromacil | Herbicide |
| Bromadiolone | Rodenticide |
| Bromcresol green | Indicator |
| Bromcresol purple | Indicator |
| Bromethalinlin | Rodenticide |
| p-Bromoacetanilide | Analgesic; antipyretic |
| 3-Bromo-d-camphor | Topical counterirritant |
| Bromophos | Insecticide |
| Bromopropylate | Acaricide |
| 5-Bromosalicylhydroxamic acid | antibacterial (tuberculostatic) |
| 5-Bromosalycilic acid acetate | Analgesic |
| Bromosaligenin | Anti-inflammatory |
| Bromthymol blue | Indicator |
| Broxyquinoline | Antiseptic; disinfectant |
| Bucetin | Analgesic |
| Bumadizon | Analgesic; anti-inflammatory; antipyretic |
| Bupirimate | Fungicide |
| Busulfan | Carcinogen, insect sterilant, antineoplastic |
| Butamben | Topical anesthetic |
| Butrylin | Insecticide |
| Butylated hydroxyanisole | Antioxidant (BHA) |

TABLE I-continued

Water-Insoluble Particulates For Binding

| Name | Function |
|---|---|
| Butyl paraben | Pharmaceutic aid; food preservative |
| 4-tert-Butylphenyl salicylate | Light absorber |
| Cacotheline | Indicator |
| Cactinomcin | Antineoplastic |
| Cadmium salycilate | Antiseptic |
| Calamine | Skin protectant |
| Calcium carbonate | Antacid |
| Calcium saccharate | Pharmaceutic aid |
| Calcium tartrate | Preservative; deodorant; antacid |
| Cambendazole | Anthelminthic |
| Candicidin | Topical antifungal |
| Candidin | Topical antifungal |
| Capsaicin | Topical analgesic |
| Captan | Fungicide; bacteriostat |
| Carbadox | Antimicrobial |
| Carbamazepine | Anticonvulsant; analgesic |
| Carbarsone | Antiamebic |
| Carbaryl | Contact insecticide |
| Carbazochrome salycilate | Antihemorrhagic |
| Carbendazim | Fungicide |
| Carbochloral | Hypnotic |
| Carbophenothion | Miticide; insecticide |
| Carboquone | Antineoplastic |
| Carisoprodol | Skeletal muscle relaxant |
| Carthamin | Dye |
| Carvacrol | Disinfectant |
| Cephalin | Local hemostatic |
| Chalcomycin | Antibiotic |
| Chartreusin | Antibiotic |
| Chitin | Vulnerary |
| Chloramben | Herbicide |
| Chloramphenacol palmitate | Antimicrobial |
| Chloranil | Fungicide |
| Chlorbetamide | Antiamebic |
| Chlordimeform | Insecticide |
| Chlorfenac | Herbicide |
| Chlorfenethol | Acaricide |
| Chlorhexidine | Topical antibacterial |
| Chloroazodin | Antibacterial; topical anesthetic |
| Chlorophacinone | Anticoagulant rodenticide |
| p-Chlorophenol | Antiseptic |
| Chlorothricin | Antibiotic |
| Chlorotrianisene | Estrogen |
| Chloroxylenol | Antiseptic; germicide |
| Chlorphenesin | Topical antifungal |
| Chlorphenesin carbamate | Relaxant (skeletal muscle) |
| Chlorphenoxamide | Antiamebic |
| Chlorpropamide | Antidiabetic |
| Chlorpyrifos | Insecticide |
| Chlorquinaldol | Topical antibacterial |
| Chlorsulfuron | Herbicide |
| Chlorothion | Insecticide |
| Chlozoxazone | Relaxant |
| Cholesterol | Pharmaceutic aid |
| Chromic carbonate | Pigment |
| Chromic hydroxide | Pigment |
| Chromic oxide | Abrasive |
| Chromic phosphate | Green pigment |
| Chrysamminic acid | Explosive |
| Chrysarobin | Antipsoriatic |
| Cilastazol | Antithrombotic |
| Cinoxate | Sunscreen agent |

Other suitable water-insoluble particles include proteins, vitamins, zeolites and silica, each of which contains electronegative atoms, such as oxygen or nitrogen groups, or both. An example of a suitable zeolite is Abscents odor absorber available from UOP of Tarrytown, N.Y. An example of a suitable antimicrobial particle is chlorhexidine (N,N"-Bis(4-chlorophenyl)-3,12-diimino-2,4,11,13-tetraazatetradecanediimidamide). The list in Table I is by no means exhaustive as it can be readily determined for each type of particle whether it is capable of forming a hydrogen bond or a coordinate covalent bond. Many of the particles are non-absorbent, or not superabsorbent polymers.

The particles listed in Table I have chemical properties that make them suitable for binding to fibers with the binders of the present invention. The listed particles are organic or inorganic compounds that have little or no water solubility, yet have the capacity to hydrogen bond. Water solubility is preferably low, for example, less than 10 g dissolves completely in 300 ml of water at 25° C., more preferably less than about 1 g in 300 ml at 25° C. This low solubility allows the particles to remain solid, and the hydrogen-bonding capacity allows them to adhere to the fibers even in cases when an aqueous binder is used. Once bound, the particles substantially retain a discrete particulate form instead of dissolving or fusing. Hence, once bound more of the particles are discrete than fused.

Many water-soluble particles that are capable of forming hydrogen bonds or coordinate covalent bonds are suitable for use with the binders of the present invention. Some such water-soluble particles are listed in Table II with an indication of the function of the listed particles.

TABLE II

Particulates For Binding

| Name | Function |
| --- | --- |
| Ethylenediaminetetraacetic acid (EDTA) | Odor absorbent |
| disodium salt of EDTA | Chelator |
| Sodium bicarbonate | Odor absorbent/pH modifier |
| Acarbose | Antidiabetic |
| Acefylline Piperazine | Bronchodilator |
| Acenocoumarol, sodium salt | Anticoagulant |
| Acephate | Insecticide |
| Acetaminophen | Analgesic |
| Acetylleucine Monoethanolamine | Antivertigo agent |
| Acid Violet 7B | Dye/Stain |
| Acitretin | Antipsoriatic |
| Acranil | Antiprotozoal (Giardia) |
| Acriflavine | Anti-infective |
| Actaplanins | Growth stimulant |
| Algestone Acetophenide | Antiacne |
| Algin | Hemostatic |
| Almagate | Antacid |
| (−)-Ambroxide | Fragrance |
| Ambucaine hydrochloride | Local anesthetic |
| Amodiaquin | Antimalarial |
| Anabasine hydrochloride | Insecticide |
| o-Anisaldehyde | Fragrance |
| Anisomycin hydrochloride | Topical antitrichomonal |
| Aralkonium chloride | Antiseptic, germicide |
| Asiaticoside | Dermatide, wounds, burns |
| Aspartame | Non-nutritive sweetener |
| Azidoamphenicol | Antimicrobial in eye infections |
| Bebeerine | Antimalarial |
| Potassium benzoate | Preservative, antifungal |
| Benzoyl peroxide | Dermatide, antiacne |
| Benzylidene acetone | Fragrance |
| Bidrin | Insecticide |
| Biphenamine hydrochloride | Antiseborrheic |
| Bishydroxycoumarin | Anticoagulant |
| Bismuth tribromophenate | Topical antiseptic |
| Blasticidin S hydrochloride | Antimicrobial |
| Bromocresyl green | Indicator |
| Bromophenol blue | Indicator |
| Butathamine hydrochloride | Anesthetic |
| Caffeine hydrochloride | CNS Stimulant |
| Calcium ascorbate | Vitamin C/Calcium source |
| Calcium bisulfite | Germicide |
| Calcium thioglycollate | Depilatory |
| Carbachol | Ophthalmic parasympathomimetic |
| Carbowax | Ointment base |
| Cetalkonium chloride | Antibacterial |
| Cethoxonium bromide | Antiseptic |

TABLE II-continued

Particulates For Binding

| Name | Function |
| --- | --- |
| Chartreusin | Antimycobacterial |
| Chloramine-T | Topical antiseptic |
| Cinnamic acid | Fragrance |
| Cotarnine chloride | Hemostatic |
| Demercarium bromide | Topical antiglaucoma |
| D-2-deoxyribose | DNA synthesis |
| Dequalinium chloride | Antiseptic |
| Dermostatin | Anti fungal |
| Dexamethasone | Glucocorticoid |
| Diacetone acrylamide | Mfr coatings, adhesives |
| 2,4-Diamino-6-hydroxypyrimidine | Indicator of nitrates/nitrites |
| 2,4-Diaminophenol dihydrochloride | Photographic developer |
| Diamthazole dihydrochloride | Antifungal |
| Diatrizoate sodium | Diagnostic aid |
| Dibekacin sulfate | Antibacterial |
| Disodium 4',5'-dibromofluorescein | FDA approved dye |
| 3,5-Dibromo-4-hydroxybenzenesulfonic acid, sodium salt | Topical disinfectant |
| Dibromopropamidine | Cosmetic preservative |
| Diflorasone | Topical anti-inflammatory |
| Dihydroxyacetone | Artificial tanning agent |
| Diisobutyl sodium sulfosuccinate | Wetting agent/detergent |
| Dikegulac | Plant growth regulator |
| Dimethisoquin | Topical anesthetic |
| Diphenicillin sodium | Antibacterial |
| Diphetarsone | Antiamebic |
| Dipyrone | Analgesic, antipyretic |
| Diquat dibromide | Herbicide, defoliant |
| Dodine | Fungicide |
| Domiphen bromide | Topical anti-infective |
| Dulcin | Non-nutritive sweetener |
| Dymixal ® | Topical burn treatment |
| Ecognidine | Topical anesthetic |
| Edetic acid | Antioxidant |
| Edoxudine | Antiviral |
| Ellagic acid | Hemostatic |
| Endothal | Herbicide, defoliant |
| Eosine I bluish | Dye |
| Eosine yellowish | Cosmetic dye |
| Erythrosine | Food dye |
| Esculin | Skin protectant |
| Ethacridine | Antiseptic |
| Ethambutol hydrochloride | Antibacterial (tuberculostatic) |
| Ethamsylate | Hemostatic |
| Ethylidene dicoumarol | Anticoagulant |
| Ethylstibamine | Antiprotozoal |
| Euprocin dihydrochloride | Topical anesthetic |
| Fast green FCF | Food coloring |
| Fenticonazole nitrate | Topical antifungal |
| Ferric albuminate | Hematinic |
| Ferric chloride hexahydrate | Astringent, styptic |
| Ferric formate | Silage preservative |
| Ferrulic acid, sodium salt | Food preservative |
| Fluorescein, disodium salt | Diagnostic aid |
| Fluoridamid | Plant growth retardant |
| Forminitrazol | Antiprotozoal (Trichomonas) |
| Fortimicin(s) | Antibacterial |
| Foscarnet sodium | Antiviral (HIV-1) |
| Fosetyl Al | Systemic fungicide |
| Fungichromin | Topical antifungal |
| Gallic acid | Astringent, styptic |
| Gentian violet | Topical anti-infective |
| Gluconolactone | Cleaner |
| Gossypol | Rubber antioxidant |
| Heparin | Anticoagulant |
| Hexamethylolmelamine | Fireproofing agent |
| Mexamidine | Antiseptic, anti-acne |
| Homatropine | Anticholinergic (opthtalmic) |
| Hydrastinine hydrochloride | Uterine hemostatic |
| Hydrocortisone phosphate, disodium salt | Glucocorticoid |
| Hydroquinine hydrochloride hemihydrate | Depigmentor |
| Hydroxyamphetamine hydrobromide | Andregenic (opthtalmic) |
| Hydroxybutyranilide | Antioxidant |
| 3-Hydroxycamphor | Topical antipruritic |
| 1-(Hydroxymethyl)-5,5-dimethylhydantion | Cosmetic preservative |

TABLE II-continued

Particulates For Binding

| Name | Function |
| --- | --- |
| 8-Hydroxyquinoline sulfate | Antiperspirant, deodorant |
| Iodic acid | Astringent |
| Itraconazole | Antifungal |
| Kanamycin(s) | Antibacterial |
| Kermesic acid | Dye |
| Kojic acid | Flavor enhancer |
| Laccaic acid | Crimson dye |
| Lactic acid | Acidulant |
| Litmus | Indicator |
| L-Lysine L-glutamate | Flavor additive |
| Lyxoflavine | Feedstuff, growth-promoter |
| Maclurin | Dye |
| Malachite green | Dye |
| Maltol | Flavor enhancer |
| Maneb | Agricultural fungicide |
| Manganese acetate | Mordant |
| Meralein sodium | Topical anti-infective |

Plus a host of others, including a wide range of inorganic salts.

The list in Table II is by no means exhaustive as it can be readily determined for each type of particle whether it is capable of forming a hydrogen bond or a coordinate covalent bond. All or most of the particles are non-absorbent, or not superabsorbent polymers. Solubility of the particle in water and the binder can be easily ascertained, for example in standard chemical reference materials.

The particles listed in Table II have chemical properties that make them suitable for binding to fibers with the binders of the present invention. The listed particles are organic or inorganic compounds that are water soluble, yet have the capacity to hydrogen bond. Water solubility is preferably high. By water soluble it is meant that the particles dissolve at a rate higher than 10 g in 300 ml of water at 25° C. The range of solubilities can extend, for example, from a lower limit of 10 g in 300 ml of water at 25° C., to an upper limit in which the particle is miscible in all proportions with water at 25° C. This high solubility allows the particles to dissolve when exposed to aqueous liquids such as urine, but the hydrogen bonding capacity allows them to adhere to the fibers in the presence of binder but in the absence of aqueous liquid during use by an end user after the manufacturing process is completed. While bound, many of the particles substantially retain a discrete particulate form instead of dissolving or fusing, at least until they are exposed to an aqueous liquid. More of the particles are discrete rather than agglomerated while bound in the absence of an aqueous liquid. If the particles are exposed to fibers with binder in liquid form, for the particles to retain their particulate form a binder is preferably selected so that the particles are sparingly soluble in the binder. By sparingly soluble it is meant that no more than about 5 g of particles dissolve in 300 ml of the binder at 25° C.

The amount of particles added to the fibers can vary widely, for example from 05 to 80 percent of the total weight of the fibrous material and particles. Antimicrobials such as chlorhexidine are effective in very low amounts, such as 0.05 percent. Superabsorbent particles are preferably added in an amount of 3–80 percent, especially 20–60 percent by weight of the fibrous materials and particles.

VI. Polymeric Binder Characteristics

The particles may be bound to the fibers by combining the particles with a polymeric binder, which may be water soluble. The polymeric binder is selected from a predetermined group of polymeric binders. The polymeric binders comprise polymeric binder molecules wherein the polymeric binder molecules have at least one hydrogen bonding functionality or coordinate covalent bond forming functionality. Preferred binders may further comprise repeating units, wherein the repeating units have such functionalities on each repeating unit of the polymer, although this is not necessary for adequate binder functions. In accordance with the present invention, the predetermined groups of polymeric binders include the group of binders consisting of polyglycols [especially poly(propyleneglycol)], a polycarboxylic acid, a polycarboxylate, a poly(lactone) polyol, such as diols, a polyamide, a polyamine, a polysulfonic acid, a polysulfonate, and combinations thereof. Specific examples of some of these compounds, without limitation, are as follows: polyglycols may include polypropylene glycol (PPG) and polyethylene glycol (PEG); poly(lactone) polyols include poly(caprolactone) diol and poly(caprolactone) triol; polycarboxylic acids include polyacrylic acid (PAA) and polymaleic anhydride; polyamides include polyacrylamide or polypeptides; polyamines include polyethylenimine and polyvinylpyridine; polysulfonic acids or polysulfonates include poly(sodium-4-styrenesulfonate) or poly(2-acrylamido-methyl-1-propanesulfonic acid; and copolymers thereof (for example a polypropylene glycol/polyethylene glycol copolymer). The polymeric binder typically has repeating units. The repeating unit may be the backbone of a compound, such as with a polypeptide, wherein the repeating polyamides occur in the peptide chain. The repeating unit may also refer to units other than backbones, for instance repeating acrylic acid units. In such a case, the repeating units may be the same or different. The binder has a functional group capable of forming a hydrogen bond or a coordinate covalent bond with particles, and a functional group capable of forming a hydrogen bond with the fibers.

As used herein, a polymer is a macromolecule formed by chemical union of 5 or more identical or different combining units (monomers). A polyamine is a polymer that contains amine functional groups and a polyamide is a polymer that contains amide functional groups. Each of the binders has a hydrogen bonding or a coordinate covalent bonding functionality, and each of the binders may have such functionalities on each repeating unit (monomer) of the polymer. This repeating functionality may be a hydroxyl, a carboxyl, a carboxylate, a sulfonic acid, a sulfonate, an amide, an ether, an amine or combinations thereof. These binders are capable of forming hydrogen bonds because they have a functional group that contains an electronegative element, such as oxygen or a nitrogen.

The polyglycol has repeating ether units with hydroxyl groups at the terminal ends of the molecule. The polycarboxylic acid, such as polyacrylic acid, has a repeating carboxyl group in which a hydrogen is bound to an electronegative oxygen, creating a dipole that leaves the hydrogen partially positively charged. The polyamide (such as a polypeptide) or polyamine has a repeating NR group in which a hydrogen may be bound to an electronegative nitrogen that also leaves the hydrogen partially positively charged. The hydrogen in both cases can then interact with an electronegative atom, particularly oxygen or nitrogen, on the particle or fiber to form a hydrogen bond that adheres the binder to the particle and fiber. The electronegative oxygen or nitrogen of the binder also can form a hydrogen bond with hydrogenatoms in the particle or fiber that have positive dipoles induced by electronegative atoms, such as oxygens or nitrogens, to which the hydrogen is attached. The polyamide also has a carbonyl group with an electronegative oxygen that can interact with hydrogen atoms in the particles or fibers. Thus, the polymeric binders can enhance the hydrogen bonding (a) between the fibers and binder; and (b) in the case of particles with hydrogen bonding functionalities, between the binder and the particles.

Alternatively, the polymeric binder may form a coordinate covalent bond with the particles and a hydrogen bond to the fibers. For example, the oxygen or nitrogen on the binder has an unbound pair of electrons that can be donated to an empty orbital in the particle to form a coordinate covalent bond. For example, one free pair of electrons on the oxygen or nitrogen can be donated to the empty p orbital of a boron-containing particle to form a coordinate covalent bond that adheres the particle to the binder. The fibers themselves contain functional groups that can form hydrogen bonds with the binder, and allow the binder to adhere to the fiber. Cellulosic and synthetic fibers, for example, may contain hydroxyl, carboxyl, carbonyl, amine, amide, ether and ester groups that will hydrogen bond with the hydroxyl, carboxylic acid, carboxylate, amide or amine groups of the binder. Hence, the polymeric binder will adhere the particle with a coordinate covalent bond and the fiber will adhere with a hydrogen bond.

In some preferred embodiments, the polymeric binder is bound to both the fibers and the particle by hydrogen bonds. A polypropylene glycol binder, for example, can be used to bind water-insoluble polyacrylate hydrogel particles to cellulosic fibers. The hydroxyl and ether groups on the glycol binder participate in hydrogen-bonding interactions with the hydroxyl groups on the cellulose fibers and the carboxyl groups on the polyacrylate hydrogel, as shown below:

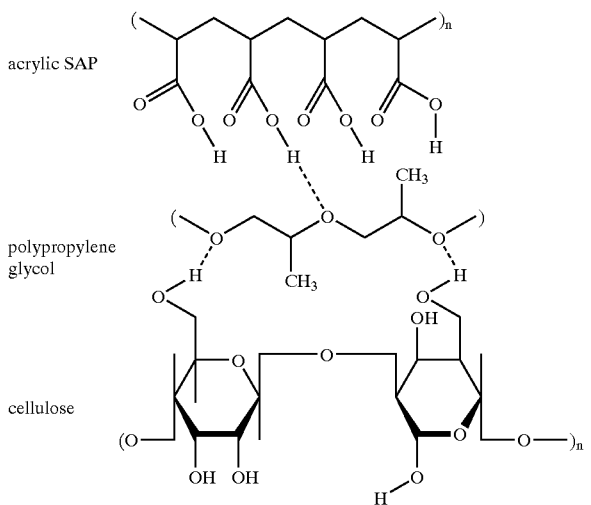

Alternatively, a polypropylene glycol (PPG) binder, for example, can be used to bind a water-soluble particle to cellulosic fibers. The hydroxyl and ether groups on the glycol binder participate in hydrogen bonding interactions with the hydroxyl groups on the cellulose fibers and appropriate functionalities on the water-soluble particle, as shown on page 41.

Hence, the binder will adhere both the particle and fiber with hydrogen bonds. The presence of a hydrogen-bonding functionality on each repeating unit of the polymeric binder has been found to increase the number of hydrogen bonding interactions per-unit-mass of polymer, which provides superior binding efficiency and diminishes separation of particles from the fibers. The repeating ether functionality On the glycol binder provides this efficiency in the examples diagrammed above. A repeating carboxyl group is the repeating functionality on polyacrylic acid, while repeating carbonyls and NR groups (wherein R is either an H or

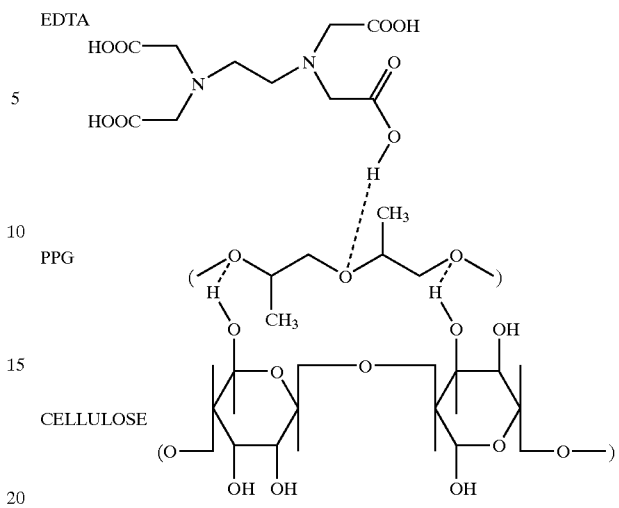

alkyl, preferably lower alkyl i.e., less than five carbon atoms, in a normal or iso configuration) of the amide linkages are the repeating functionalities on polyamides such as polypeptides. A repeating amine group is present on polyamines.

The polymeric organic binders of the present invention are expected to increase in binding efficiency as the length of the polymer increases, at least within the ranges of molecular weights that are reported in the examples below. This increase in binding efficiency would be attributable to the increased number of hydrogen bonding or coordinate covalent bonding groups on the polymer with increasing molecular length. Each of the polymeric binders has a hydrogen bonding or coordinate covalent bonding functionality, and each such binder may have such functionalities on each repeating unit of the polymer. Hence, longer polymers provide more hydrogen bonding groups or coordinate covalent bonding groups that can participate in hydrogen-bonding interactions or in coordinate covalent bonds.

Although the invention is not limited to polymeric binders of particular molecular weights, polymeric binders having a molecular weight greater than 500 grams/mole are preferred because they provide attractive physical properties, and the solid is less volatile as compared to low-molecular-weight polymeric binders. Polymeric binders with molecular weights greater than 4000 grams/mole are especially preferred because they have minimal volatility and are less likely to evaporate from the particles. Low-molecular weight materials typically are more mobile than are the higher-molecular weight materials. Low-molecular weight materials can more easily move to the fiber-particle interface, and are more easily absorbed by the fiber, thus making them less available to bond the particles to the fibers. The higher molecular weight materials are less apt to be absorbed by the fibers, and are less volatile than the low-molecular weight materials. As a result, higher molecular weight polymeric binders, to a greater extent, remain on the surface of the particles where they are more available to bond particles to fibers. In some particular embodiments, polymers with molecular weights between 4000 and 8000 grams/mole have been used. Polymers with molecular weights above 8000 may be used, but such exceedingly high molecular weight polymers may decrease binding efficiency because of processing difficulties.

Certain polymeric binders have greater binding efficiency because their repeating functionality is a more efficient hydrogen bonding group. It has been found that repeating amide groups are more efficient than repeating carboxyl functionalities, which are more efficient than repeating hydroxyl functionalities, which in turn are more efficient than amine or ether functionalities. Hence, polymeric binders may be preferred that have repeating amine or ether functionalities, more preferably repeating hydroxyl functionalities, and even more preferably repeating carbonyl or carboxyl functionalities, and most preferably repeating amide functionalities. Binding may occur at any pH, but is suitably performed at a neutral pH of 5–8, preferably 6–8, to diminish acid hydrolysis of the resulting fibrous product. Suitable binders may be selected from the group consisting of polyglycols such as polyethylene glycol or polypropylene glycol, polycarboxylic acids such as polyacrylic acid, polyamides, polyamines, poly(lactone) polyols, such as poly (caprolactone) diol, and combinations or copolymers thereof.

The group consisting of polycarboxylic acids (such as acrylic acid), polyamides and polyamines has been found to have a especially good binding efficiency. Among polyamides, polypeptides are especially preferred.

VII. Non-Polymeric Binder Characteristics

The particles may be bound to the fibers by a non-polymeric organic binder selected from a predetermined group of binders that each have a volatility less than water. The vapor pressure of the binder may, for example, be less than 10 mm Hg at 25° C., and more preferably less than 1 mm Hg at 25° C. The non-polymeric binders comprise non-polymeric binder molecules wherein the non-polymeric binder molecules have at least one functional group that forms hydrogen bonds or coordinate covalent bonds with the particles. In accordance with the present invention, the predetermined group of non-polymeric binders may include a functional group selected from the group consisting of a carboxyl a carboxylate, a carbonyl, a sulfonic acid, a sulfonate, a phosphate, a phosphoric acid, a hydroxyl, an amide, an amine, and combinations thereof (such as an amino acid or a hydroxy acid) wherein each binder includes at least two such functionalities, and the two functionalities are the same or different. A requirement for the non-polymeric binder is that it have a plurality of functional groups that are capable of hydrogen bonding, or at least one group that can hydrogen bond and at least one group that can form coordinate covalent bonds. As used herein, the term "non-polymeric" refers to a monomer, dimer, trimer, tetramer, and oligomers, although some particular non-polymeric binders are monomeric and dimeric, preferably monomeric.

Particularly preferred non-polymeric organic binders are capable of forming five or six membered rings with a functional group on the surface of the particle. An example of such a binder is an amine or amino acid (for example, a primary amine or an amino acid such as glycine) which forms six-membered rings by forming hydrogen bonds:

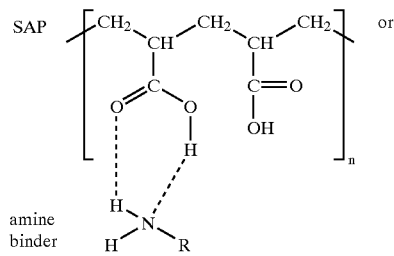

-continued

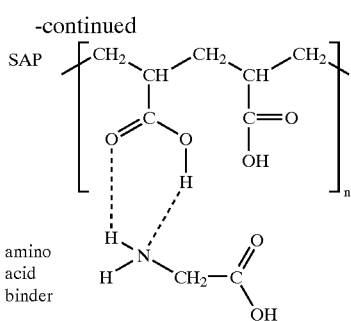

A six-membered ring also is formed by the hydroxyl groups of carboxylic acids, alcohols, and amino acids, for example:

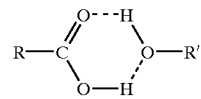

A five-membered ring can be formed by the binder and the functionality on the surface of the particle, for example:

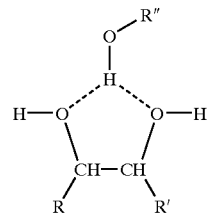

wherein the particle is a water-insoluble particle such as SAP and the binder is an alcohol, such as a polyol with hydroxyl groups on adjacent carbos, such as a butylene glycol, for example, 2,3-butanediol. A binder that forms a five-membered ring can also be used with a water-soluble particle, for example, wherein the particle is EDTA and the binder is an alcohol, such as a polyol with hydroxyl groups on adjacent carbons, such as a butylene glycol, for example, 2,3-butanediol.

Other alcohols that do not form a five-membered ring also can be used, for example alcohols that do not have hydroxyl groups on adjacent carbons. Examples of suitable alcohols include primary, secondary or tertiary alcohols.

Amino alcohol binders are alcohols that contain an amine group (—NR$_2$), and include binders such as ethanolamine (2-aminoethanol), and diglycolamine (2-(2-aminoethoxy) ethanol)). Non-polymeric polycarboxylic acids contain more than one carboxylic acid functional group, and include such binders as citric acid, propane tricarboxylic acid, maleic acid, butanetetracarboxylic acid, cyclopentanetetra-carboxylic acid, benzene tetracarboxylic acid and tartaric acid. A polyol is an alcohol that contains a plurality of hydroxyl groups, and includes diols such as the glycols (dihydric alcohols) ethylene glycol, propylene glycol and trimethylene glycol; triols such as glycerin (1,2,3-propanetriol); esters of hydroxyl containing binders may also be used, with mono- and di-esters of glycerin, such as monoglycerides and diglycerides, being especially preferred; and polyhydroxy or polycarboxylic acid compounds such as tartaric acid or ascorbic acid (vitamin C):

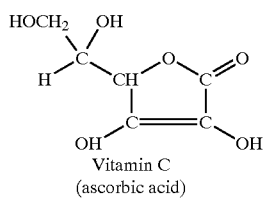

Vitamin C
(ascorbic acid)

Hydroxy acid binders are acids that contain a hydroxyl group, and include hydroxyacetic acid ($CH_2OHCOOH$) and lactic, tartaric, ascorbic, citric, and salicylic acid. Amino acid binders include any amino acid, such as glycine, alanine, valine, serine, threonine, cysteine, glutamic acid, lysine, or β alanine.

Sulfonic acid binders and sulfonates are compounds that contain a sulfonic acid group ($—SO_3H$) or a sulfonate ($—SO_3^-$). Amino-sulfonic acids also can be used. One example of an amino-sulfonic acid binder suitable for the present invention is taurine, which is 2-aminoethanesulfonic acid.

Non-polymeric polyamide binders are small molecules (for example, monomers or dimers) that have more than one amide group, such as oxamide, urea and biuret. Similarly, a non-polymeric polyamine binder is a non-polymeric molecule that has more than one amine group, such as ethylene diamine, EDTA or the amino acids asparagine and glutamine.

Although other non-polymeric organic binders are suitable in accordance with the discussion above, the non-polymeric organic binder is preferably selected from the group consisting of glycerin, a glycerin monoester, a glycerin diester, glyoxal, ascorbic acid, urea, glycine, pentaerythritol, a monosaccharide, a disaccharide, citric acid, taurine, tartaric acid, dipropyleneglycol, an urea derivative, phosphate, phosphoric acid, and combinations thereof (such as hydroxy acids). The non-polymeric binder also is most preferably selected from the group consisting of glycerin, a glycerin monoester, a glycerin diester, a polyglycerin oligomer, a propylene glycol oligomer, urea and combinations thereof (such as glycerin and urea). As used herein, an oligomer refers to a condensation product of polyols, wherein the condensation product contains less than ten monomer units. A polyglycerin oligomer as referred to herein means a condensation product of two or more glycerin molecules. A propylene glycol oligomer as referred to herein means a condensation product of two or more propylene glycol molecules. The non-polymeric binders also preferably include functionalities selected from the group consisting of a carboxyl, a carboxylate, a carbonyl, a sulfonic acid, a sulfonate, a phosphate, a phosphoric acid, a hydroxyl, an amine, an amide, and combinations thereof (such as amino acids and hydroxy acids). The non-polymeric binders may have at least two functionalities from such group, and the groups may be the same or different.

Each of the non-polymeric binders disclosed above is capable of forming hydrogen bonds because it has a functional group that contains electronegative atoms, particularly oxygens or nitrogens, or has electronegative groups, particularly groups containing oxygens or nitrogens, and that also may include a hydrogen. An amino alcohol, amino acid, carboxylic acid, alcohol and hydroxy acid all have a hydroxyl group in which a hydrogen is bound to an electronegative oxygen, creating a dipole that leaves the hydrogen partially positively charged. The amino alcohol, amino acid, amide and amine all have an NR group in which a hydrogen may be bound to an electronegative nitrogen that also leaves the hydrogen partially positively charged. The partially positively charged hydrogen in both cases then can interact with an electronegative element, such as oxygen or nitrogen, on the particle or fiber to help adhere the binder to the particle and fiber. The polycarboxylic acid, hydroxy acid, amino acid and amide also have a carboxyl group with an electronegative oxygen that can interact with hydrogen atoms in the particles and fibers, or in intermediate molecules between the binder and particles or fibers. Similarly, electronegative atoms (such as oxygen or nitrogen) on the fiber or particle can interact with hydrogen atoms on the binder that have positive dipoles, and partially positive hydrogen atoms on the fiber or particle can interact with electronegative atoms on the binder.

Several proposed hydrogen bonding interactions of two of the binders (glycine and 1,3-propanediol) with cellulose are shown below:

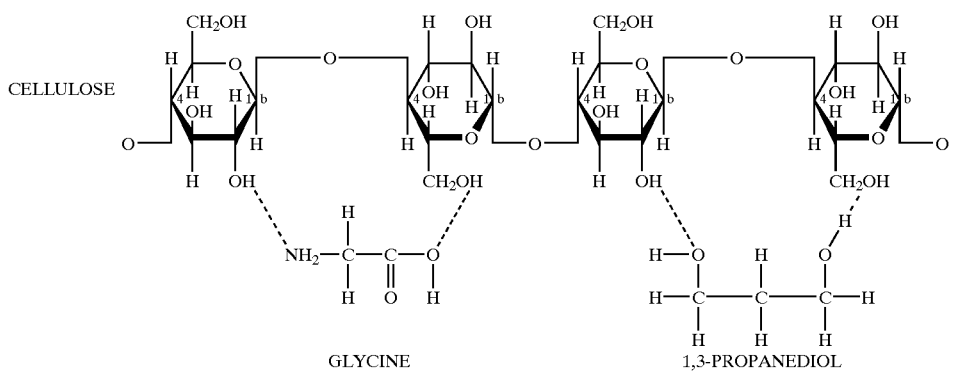

The hydrogen bonding interactions are shown as dotted lines. One such interaction is shown between the nitrogen of glycine and a hydrogen of an —OH on cellulose. A hydrogen bond with glycine is also shown between an oxygen of the —OH on glycine and the hydroxy hydrogen of an alcohol sidechain on cellulose. Hydrogen bonding interactions of the 1,3-propanediol are shown in dotted lines between an oxygen on an —OH group of the binder and a hydrogen of an —OH group on the cellulose molecule. Another hydrogen bond is also shown between a hydrogen on an —OH group of the glycol binder and an oxygen in an alcohol side chain of the cellulose.

It also is possible for water or other hydrogen bonding molecules to be interposed between the fiber and binder, such that the fiber and binder are both hydrogen bonded to the water molecule.

Alternatively, an atom on the binder may have an unbound pair of electrons, such as a lone pair of electrons from an oxygen or nitrogen atom, that can be donated to an empty orbital of an acceptor atom in the particle to form a coordinate covalent bond. The free pair of electrons on the oxygen or nitrogen can be donated to the empty p, d or f orbital of a particle (for example a boron-containing particle) to form a coordinate covalent bond that adheres the particle to the binder. The fibers themselves do not normally contain functional groups that can act as electron acceptors in the formation of coordinate covalent bonds with the binders, but hydrogen bonding interactions allow the binder to adhere to the fiber. Cellulosic and synthetic fibers, for example, contain hydroxyl, carboxyl and ester groups that will hydrogen bond with the hydroxyl, carboxylic acid, amide, amine, or other groups of the binder. Non-cellulosic or non-synthetic fibers that have these functionalities also can be used, for example silk, which has an amide linkage. Hence the binder will adhere the particle with a coordinate covalent bond and the fiber with a hydrogen bond.

In some preferred embodiments, the binder is bound to both the fibers and the particle by hydrogen bonds. A polyol binder, such as a diol, for example, can be used to bind polyacrylate hydrogel particles to cellulosic fibers. The hydroxyl groups on the polyol binder participate in hydrogen-bonding interactions with the hydroxyl groups on the cellulose fibers and the carboxyl groups on the polyacrylate hydrogel. Hence, the binder will adhere to both the particle and fiber with hydrogen bonds. These hydrogen bonds provide excellent binding efficiency and diminish separation of bound particles from the fibers.

A structural drawing is shown below in which citric acid, vitamin C and urea adhere water-insoluble SAP particles to cellulose with hydrogen bonds, or water-soluble EDTA particles. Some of the possible hydrogen bonding interactions are shown as dashed lines. It is possible that other molecules (such as water molecules) also may participate in some of these bonds, for example, as an intermediary between the binder and particle or fiber.

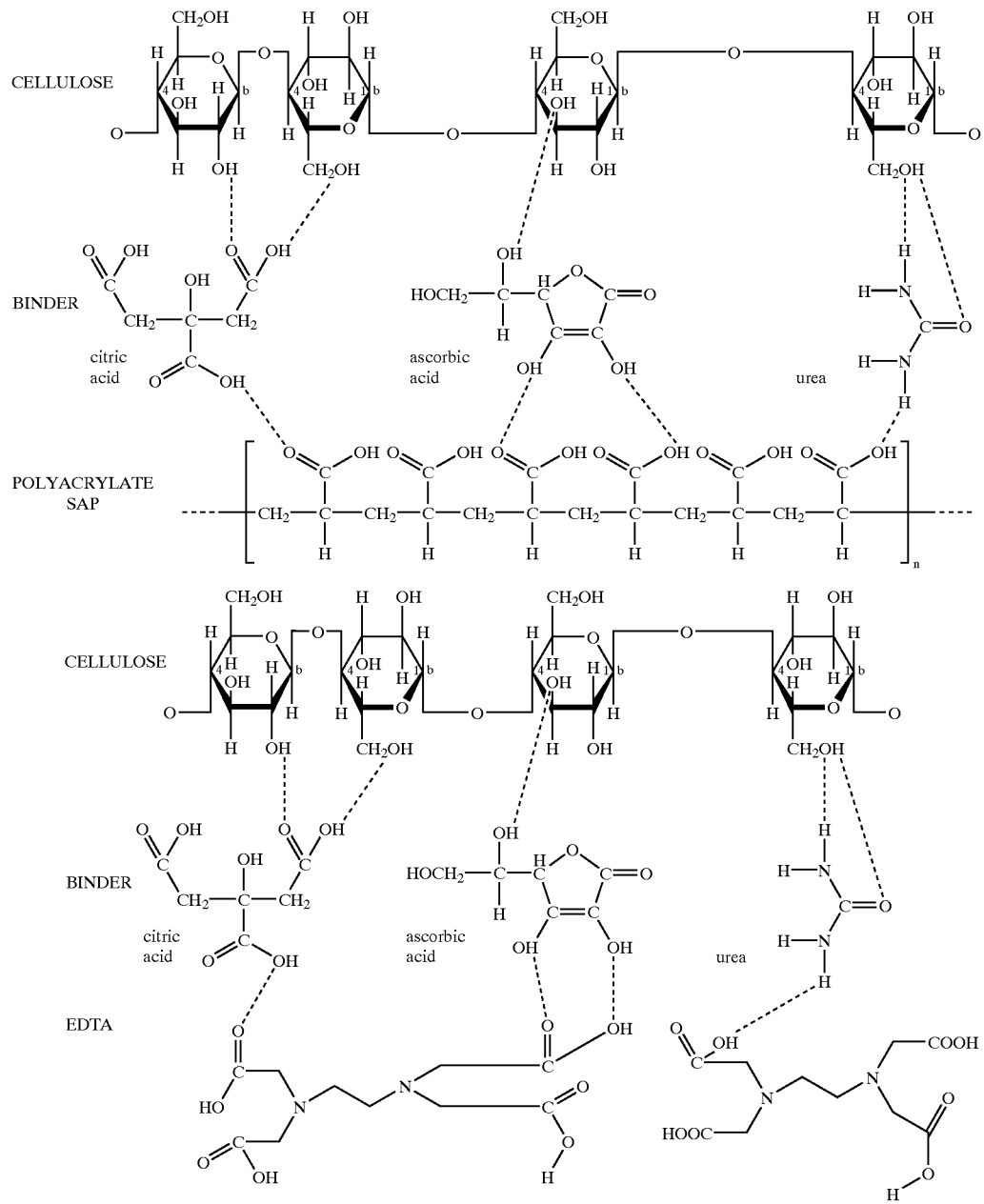

Particularly efficient hydrogen bonding binders include those with carboxyl groups, such as ascorbic acid, or amide groups, such as urea. Hydroxyl groups are also very efficient binders. Amine and ether functionalities are less efficient binders.

Binders have functional groups that may be selected independently or in combination from the group consisting of a carboxyl, a carboxylate, a carbonyl, a hydroxyl, a sulfonic acid, a sulfonate, a phosphoric acid, a phosphate, an amide, an amine, and combinations thereof. These functional groups might be provided by the following exemplary chemical compounds: a carboxyl group could be provided by carboxylic acids, such as ascorbic acid; a carboxylate, which is an ionized carboxylic acid, could be provided by a material such as potassium citrate; a carbonyl group can be provided by an aldehyde or ketone; a hydroxyl can be provided by an alcohol or polyol, such as glycerol, or a mono- or diglyceride, which are esters of glycerol; an amide, such as a urea; and an amine, which may be provided by an alkyl amine, such as ethanolamine, wherein the binder has at least two of these functional groups, and each of the functional groups can be the same (for example, a polyol, polyaldehyde, polycarboxylic acid, polyamine or polyamide) or different (for example, an amino alcohol, hydroxy acid, hydroxyamide, carboxyamide, or amino acid). Functional groups also may be selected independently or in combination from the group consisting of carboxyl, an alcohol, an amide and an amine. An aldehyde may optionally be a member of each of these groups, particularly if it is oxidized to a carboxylic acid.

Combinations of polymeric and non-polymeric binders may also be used, with or without other binders, providing that they are non-reactive. That is, providing that the binders do not react in a manner which prevents the binders from possessing the functional groups required to be present for binding in accordance with the present invention.

VIII. Process Advantages

The binders of the present invention also provide numerous process advantages. Binding of particles to the fibers can occur, for example, without external application of heat. Hence, if desired, particle binding may occur at ambient temperature. The present invention therefore is distinct from prior-art crosslinking processes in which elevated temperatures are required to covalently crosslink cellulose groups to one another. Moreover, the binders of the present invention have the advantage of being reactivatable by addition of a fluid, such as a liquid solvent (sometimes referred to herein as a reactivation liquid, one example of which is water). Hence, a liquid binder (which would include a solution of a solid or liquid binder, or a binder that has a melting point below room temperature) can be applied to particles and the binder allowed to air dry, for example until the particles reach an equilibrium moisture content with the moisture in the ambient air. The binder, which at least partially coats the particle, may then be reactivated in the presence of fibers to bind the particles in place. Some of the binders (especially the liquid binders) may, after the particles are bound to fibers, diffuse throughout the fibers to reach an equilibrium distribution of the binder. Alternatively, the binder can be combined with the particles as a solid, for example as particles or a powder. At a later stage of processing, water or another activating fluid or liquid may be added to the combined binder and particles. The particles with activated binder then may be added to the mat and adhered, for example to target areas of a fiber mat. Alternatively, the particles and partially coating binder may be added to the mat prior to or simultaneously with activation of the binder.

The binders may be liquids at room temperature (such as glycerin), or liquid solutions of binders that are solids at room temperature (for example, an aqueous solution of glycine), or liquid hot melts of solid binders. Solid binders may be blended with particles in particulate form, provided they are fixed or adhered to the fibers at a later time, for example by the subsequent application of heat, pressure, or liquid.

The binding reaction of the present invention can occur across a broad range of pH without requiring a catalyst. A suitable pH range without a catalyst is 1–14, but preferred ranges are 5–8 or 6–8 because such neutral pH ranges will produce fibrous products (such as cellulose products) that are less prone to damage by acid hydrolysis. A non-acidic pH (7 or greater) will provide an environment that inhibits formation of ester bonds, and promotes formation of the hydrogen bonds or coordinate covalent bonds that adhere the particles of the present invention to the fibers with the binder.

When water-insoluble particles are used, the moisture content of the fibers during the binding reaction is 0.5–50%, suitably 5–40%, or preferably 5–20% water by weight of the fibers, binder and particle. A moisture-content greater than 20%, preferably 30%, or in the range 20–50%, or 30–50%, can be used even though such high moisture contents interfere with intermediate anhydride formation and inhibits formation of covalent bonds in the production of high-bulk crosslinked fibers. When water-soluble particles are used, the moisture content of the fibers during the binding reaction is 0.5–30%, suitably 5–25%, preferably 12–20%. Particles may be added to the fibers with the particles distributed throughout a fibrous product without being confined to a surface of the product. The particles can be distributed throughout the depth of a fiber product such as a mat or web.

The binder suitably is present in an amount of at least 0.01 percent, and no more than 80 percent, by weight of the particles ("percent by weight"). In especially preferred embodiments, the binder is present in an amount of 0.03 to 50 percent, preferably 0.03 to 20 percent, more preferably 0.03 to 5 percent, and even more preferably 0.03 to 1 percent by weight of the particles. Below about 0.01 percent when combined with the particles, an insufficient amount of binder is present to achieve adequate binding. Using excessive amounts of binder can introduce unnecessary expense into the binding process. High percentages of binder can also cause processing problems because the binder material transfers to equipment surfaces. Therefore, it is often preferred to use no more binder than is required to bind the particles and fibers.

Thermoplastic binders also may be used to help bind fibers to each other and particles to fibers. The binder that has the hydrogen bonding or coordinate covalent bonding functionalities itself may be thermoplastic. The polymeric binders and some non-polymeric binders of the present invention have the advantage of being thermoplastic or meltable solids. Hence, particles treated with such binders in accordance with the present invention may be thermobonded by elevating the fiber temperature above the melting temperature of the binder to melt or soften the thermoplastic binder and physically bind the particles to the fibers and to a limited extent (unless high percentage of binders are used) the fibers to each other. Alternatively, an auxiliary or second binder can be applied to the fibers as a solid at room temperature, and the temperature of the second binder elevated above its melting point to thermobond the fibers and particles. The auxiliary binder may be applied to the fibers either before or after the primary binder containing particles are combined with the fibers, but before thermobonding.

The particles with binders of the present invention may be used with fibers that have substantial intrafiber covalent crosslinks (such as HBA available from Weyerhaeuser) or fibers which are substantially free of intrafiber covalent crosslinking. Examples of individualized intrafiber crosslinked fibers are seen in European Patent Applications 440 472 A1 and 427 317 A2, which produce products that those publications describe as being substantially free of interfiber bonds. The fibers of the present invention do not need to be processed as in those European applications to eliminate interfiber bonds. Particles at least partially coated with binders of the present invention can therefore be used with natural fibers that have substantial interfiber bonding, which are defined as fibers that have not been processed as in European Applications 440 472 A1 and 427 317 A2 to substantially eliminate interfiber bonds. Cellulose fibers that have not been so processed are substantially free of intrafiber bonds.

The fibrous product of the present method (with or without intrafiber crosslinking) may further be densified by external application of pressure. The densified product is compact and easily transported. And, when the particles are superabsorbent particles, the resulting fibrous product has superior absorbent properties as compared to nondensified products. The inventors have found that the binders of the present invention produce a product that can be easily densified. Easy densification is associated with the hydrogen bonds and coordinate covalent bonds formed between the binder and the particles and fibers. The fibers are particularly easily densified when at least 5% by weight of the fibers, particles and binder, more preferably 10%, are particles adhered to the fibers. Moreover, densification appears to be facilitated by using superabsorbent particles, and even more suitably densifying using superabsorbent particles at least partially coated with an active binder as the time densification occurs.

In accordance with this invention, the binders may be applied to particles before, or simultaneously with, addition of the particles to the fibers. A preferred approach is to simply spray, as by a mist or fog, the binder onto the particles as the particles are delivered to the fibers. Simultaneous addition can be accomplished by two separate streams of particles and binder that are simultaneously directed at a fibrous substrate, or alternatively merged immediately or some time prior to impacting against the substrate. Some of the binder may reach the fibers without impacting a particle, but the bulk of the particles will be at least partially coated with the binder. Without limiting the invention, it appears that the addition of small amounts of moisture to the particles may help bind superabsorbent particles and perhaps other types of particles to the fibers. For example, exposing the particles to air at 65 percent humidity as they are delivered to binder coated particles may enhance the particle bonding to the fibers.

Binding may be performed under conditions that favor formation of hydrogen bonds or coordinate covalent bonds, and discourage formation of covalent bonds. Conditions that favor covalent bonds are those disclosed in U.S. Pat. Nos. 4,412,036 and 4,467,012 wherein particle and binder would be laminated between tissue layers under high temperature and pressure to form laminated adherent tissue layers. That patent teaches that minimal adhesion occurs at 200 pli (pounds per linear inch, as in a calendar press) if no external heat is supplied, but adhesion improves as the reaction temperature increases. Improved adhesion of the tissue layers occurs because of enhanced covalent bonding as the temperature increases.

Conditions that favor covalent bond formation are also shown in European Patent Applications 440 472 A1; 427 317 A2; 427 316 A2; and 429 112 A2. These European publications use polycarboxylic acid crosslinkers, and require elevated temperatures (for example above 145° C.) and acidic conditions (pH less than 7) to promote formation of intrafiber covalent ester bonds and inhibit reversion of the ester bonds. The present invention, in contrast, can form hydrogen or coordinate covalent bonds below 145° C., below 100° C., and even at room temperature. The binders of the present invention also can bind particles to fibers under neutral or alkaline conditions, i.e., at a pH above 7, but preferably at a pH of 5–8 or 7–8. Fibers that have high bulk as a result of intrafiber covalent crosslinks are prepared by individualizing the fibers (for example, in a fiberizer) and curing them at an elevated temperature (above 150° C.). Initial application of the binder-coated particles on such high-bulk fibers preferably occurs after the curing step, particularly if the binder is capable of functioning as a crosslinking material. The specific types of binders disclosed herein that also can crosslink are polyols, polyaldehydes, polycarboxylic acids, and polyamines (polymeric or nonpolymeric binders with more than one amine group). If such binders are present during curing, the binder that is in contact with the fiber will tend to be consumed during the curing step to form covalently crosslinked bonds. By consumed it is meant that the hydrogen bonding sites on the binder tend to be used up so that they are no longer available for bonding the particles via the binder to the fibers. Thus, when this occurs, the binder is no longer available for hydrogen bonding or coordinate covalent bonding, and particle binding to fibers is ineffective.

The intrafiber covalent bond forming processes described in the above European publications require formation of an anhydride that then reacts with a hydroxy group on cellulose to form a covalent ester bond. The presence of more than about 20% water by weight in the fibers is believed to retard the formation of the anhydride and inhibits covalent bond formation.

Hence, in processes that use polycarboxylic acids, polyols and polyamines (which includes both polymeric and nonpolymeric amines having more than one amine group) as binders on the particles in the present invention, the fibers should contain at least 20% water (or 20–50% water) by weight if the particles and binder are present in the fibers when curing occurs. The water retards covalent bond formation, and is expected to prevent all of the binder on the particles from being used to form covalent intrafiber crosslinks. Hence, some of the binder remains available to form the bonds with the fibers and produce ease of densification in fiber products made by the process of the present invention.

The present invention, in contrast, produces a product under conditions that favor formation of hydrogen or coordinate covalent bonds. Hence, the particles can be bound to the fibers in the absence of the external application of heat or pressure. Particles also may be bound and the resulting fiber product densified, for example at less than 200 pli (about 8000 psi) with SAP, or less than 100 pli (about 4000 psi) with SAP, in the absence of external application of heat to produce a product in which a substantial portion of the particles are bound by non-covalent bonds (hydrogen or coordinate covalent bonds). A substantial portion of particles bound by non-covalent bonds means at least half of the bonds binding particles to fibers are other than covalent bonds, for example, hydrogen or coordinate covalent bonds.

In yet other examples, particles may be bound in the absence of external application of pressure, but at elevated temperatures.

In particularly preferred embodiments, the particles are substantially entirely bound to the fibers non-covalently.

IX. Binding Examples for Polymeric Binders and Water-Insoluble Particles

Several examples are provided below to illustrate using the polymeric binders within the present invention to attach superabsorbent particles to southern bleached kraft pulp.

EXAMPLE 1

A 321 gram amount of NB-416 southern bleached kraft fluff obtained from Weyerhaeuser Company may be air-entrained in a blender-like mixing device. 5 grams of poly(caprolactone) diol (average molecular weight 2000, supplied by Aldrich Chemical Company of Milwaukee, Wisc.) dissolved in 5 ml of deionized water may be sprayed as a binder onto 435 grams of starch graft polyacrylate hydrogel fines (IM 1000F; supplied by Hoechst-Celanese of Portsmouth, Va.) as the fines are added to the blender and mixed therein. The product may then be removed from the blender, and spread out in a fume hood to air dry overnight. The resulting product may then be airlaid on a small airlay line, from M & J Machines (of Horsens, Denmark) and thermobonded at 140° C. for one minute to produce a web containing superabsorbent particles (SAP) attached to the individualized fibers. This binder has a low melting point, hence raising the temperature to 140° C. melted the binder and allows it to flow to some extent over the fibers and particles to enhance hydrogen bonding interactions and provide mechanical encapsulation that further binds the fibers and particles. This is also an example of activating a solid binder by heating it, without liquid addition. A polypropylene glycol/polyethylene glycol copolymer binder would also behave in this manner.

EXAMPLE 2

A 321 gram amount of southern kraft fluff can be air-entrained in a blender-like mixing device. 15 grams of a 65% solution of polyacrylic acid (average molecular weight=2,000; supplied by Aldrich Chemical Company of Milwaukee, Wisc.) diluted with 10 ml of deionized water may be sprayed onto 435 grams of polyacrylate hydrogel (FAVOR 800 supplied by Stockhausen of Greensboro, N.C.) as the hydrogel is added into the mixing device and mixed with the fluff and polyacrylic acid binder. The product can be removed and spread out to dry and then fed to a hammermill with a three-eighths inch round hole screen and shunted to a small airlay line to produce a web containing SAP attached to the individualized fibers.

EXAMPLE 3

A 321 gram amount of southern bleached kraft fluff may be air-entrained in a blender-like mixing device and 10 grams of polyglycine (molecular weight=5,000–15,000; supplied as a dry powder by Sigma Chemical Company of St. Louis, Mo.) diluted with 10 ml of deionized water may be sprayed onto 435 grams of starch graft polyacrylate hydrogel fines (IM 1000F; supplied by Hoechst-Celanese of Portsmouth, Va.) as the particles are delivered to the blender for mixing. The product may then be removed and spread out in a fume hood to dry overnight. The resulting product may be fed into a Fitz hammermill with a three-eighths inch round hole screen and shunted to a small M & J airlay line to produce a web containing SAP attached to the fibers.

EXAMPLE 4

A 321 gram amount of southern bleached kraft fluff may be air-entrained in a blender-like mixing device and 200 grams of a 50% solution of polyethyleneimine (molecular weight=50,000–100,000; supplied by ICN Biomedicals, Inc. of Costa Mesa, Calif.), or polyvinyl pyridine may be sprayed onto 435 grams of starch graft polyacrylate hydrogel fines (IM 1000F; supplied by Hoechst-Celanese of Portsmouth, Va.) and added to the blender for mixing. The product may be removed and spread out in a fume hood to dry overnight. The resulting product may be fed into a Fitz hammermill with a three-eighths inch round hole screen and shunted to a small M & J airlay line to produce a web containing SAP attached to the fibers.

The classes of polymeric binders that encompass those described in Examples 1–4 are especially preferred over other multiple hydrogen bonding functionality polymers for a number of reasons. One important reason is that their functionalities produce very strong, effective hydrogen bonding. Other important reasons include their relative lack of reactivity (as compared with polyaldehydes or polyisocyanates) and their low toxicity (again, as compared with polyaldehydes or polyisocyanates).

EXAMPLE 5

0.03 grams of polyethylene glycol (MW 200, supplied by Aldrich, Milwaukee, Wisc.) were dropped onto 30 grams of a starch graft polyacrylate hydrogel (IM 3900; supplied by Hoeschst Celanese, Portsmouth, Va.) and the resulting mixture was air entrained in a blender-like mixing device for 30 seconds to ensure complete mixing. 1.2 grams of a southern bleached kraft pulp sheet (NB 416; supplied by Weyerhaeuser, Tacoma, Wash.) were fiberized in a Waring blender. While the blender was running, 0.80 grams of the PEG-treated hydrogel were added to the fluff. The blender was then stopped and the mixture was removed. The resulting product was examined by a light microscope and revealed fibers with attached hydrogel particles.

X. Non-Polymeric Binding Examples

Several examples are provided below to illustrate the use of several non-polymeric organic binders of the present invention to attach superabsorbent particles to southern bleached kraft pulp. Several examples of binder activation and reactivation also are provided.

EXAMPLE 6

30 grams of a starch graft polyacrylate hydrogel (IM 3900; supplied by Hoechst Celanese, Portsmouth, Va.) were treated with polyethylene glycol (MW 400, supplied by Aldrich, Milwaukee, Wisc.) as described above in Example 5. Similar results were obtained.

EXAMPLE 7

A 3171 gram amount of southern bleached kraft fluff and 4348 grams of starch graft polyacrylate hydrogel fines (IM 1000; supplied by Hoechst-Celanese of Portsmouth, Va.) were air-entrained in a blender-like mixing device and 100 grams of glycerin (96%, USP; supplied by Dow Chemical Co. of Midland, Mich.) diluted with 50 grams of deionized water, were sprayed onto mixture. The blender was stopped, the product was vacuumed out, and spread out in a fume hood to dry overnight. The resulting product was examined by scanning electron microscope and revealed superabsorbent particles attached to fibers. This example demonstrates that the fibers and particles may be simultaneously exposed to the binder to produce fibers with attached particles.

Glycerin is advantageous because it tends to penetrate the fibers and soften them in addition to binding the particles to the fibers. However, over time less glycerin is available at the surface of the particles for use in binding particles in the event the glycerin/particle material is stored for long periods prior to use in adhering to fibers (e.g. if reactivation is delayed for several weeks or more). This can be compensated for in part by using higher percentages of glycerin on the particles. Also, monoglyceride and diglyceride binders do not penetrate as readily and therefore can be stored longer before reactivation to adhere particles.

EXAMPLE 8

30 grams of a starch graft polyacrylate hydrogel (IM 3900; supplied by Hoechst Celanese, Portsmouth, Va.) were stirred into 50 grams of glycerin (Supplied by Dow chemical of Midland, Mich.) and the excess glycerin was removed by suction filtration. 1.2 grams of a southern bleached kraft pulp sheet (NB 416; supplied by Weyerhaeuser, Tacoma, Wash.) were fiberized in a Waring blender. While the blender was running, 0.80 grams of the glycerin-treated hydrogel were added to the fluff. The blender was then stopped and the mixture was removed. The resulting product was examined by light microscopy and revealed fibers with attached hydrogel particles. The glycerin level in the hydrogel particles produced in the manner described above was determined to be 61% by NMR spectroscopy.

EXAMPLE 9

0.03 grams of glycerin (96%, USP, supplied by Dow, Midland, Mich.) were dropped onto 30 grams of a starch graft polyacrylate hydrogel (IM 3900; supplied by Hoechst Celanese, Portsmouth, Va.) and the resulting mixture was air entrained in a blender-like mixing device for 30 seconds to ensure complete mixing. 1.2 grams of a southern bleached kraft pulp sheet (NB 416; supplied by Weyerhaeuser, Tacoma, Wash.) were fiberized in a Waring blender. While the blender was running, 0.80 grams of the glycerin-treated hydrogel were added to the fluff. The blender was then stopped and the mixture was removed. The resulting product was examined by light microscopy and revealed fibers with attached hydrogel particles. Aliquots of the glycerin-treated hydrogel were blended with fluff while increasing time elapsed between glycerin treatment and attempted fiber attachment. Attempts to attach fiber, solely by blending fiber with treated particles, are still successful after 10 weeks. Samples tested after longer time intervals are expected to perform similarly.

EXAMPLE 10

0.03 grams of dipropylene glycol (supplied by Aldrich, Milwaukee, Wisc.) were dropped onto 30 grams of a starch graft polyacrylate hydrogel (IM 3900; supplied by Hoechst Celanese, Portsmouth, Va.) and the resulting mixture was air-entrained in a blender-like mixing device for 30 seconds to ensure complete mixing. 1.2 grams of a southern bleached kraft pulp sheet (NB 416; supplied by Weyerhaeuser, Tacoma, Wash.) were fiberized in a Waring blender. While the blender was running, 0.80 grams of the dipropylene glycol-treated hydrogel were added to the fluff. The blender was then stopped and the mixture was removed. The resulting product was examined by light microscopy and revealed fibers with attached hydrogel particles.

EXAMPLE 11

A 900-gram amount of southern bleached kraft fluff pulp sheet can be fed into a Fitz hammermill fitted with a three-eighths-inch hole screen. The sheet can be defiberized, shunted to an M & J airlay line, and airlaid into a web. As the web emerges, target zones of the web may be dusted with particles to which a 50% solution of lactose has been applied. The target zones may be misted with water to raise the moisture content to 17–21%. The particles may comprise five gram aliquots of binder containing starch graft polyacrylate hydrogel fines (IM 1000F; supplied by Hoechst-Celanese of Portsmouth, Va.) which are sifted onto the target zones. The web that would result contains target zones with 5 grams of SAP attached to the fibers of each target zone. Portions of the web that were not moistened would not adhere the particles well. This is an example of applying the binder containing particles to a target zone so that SAP primarily adheres to the target areas where the binder was applied. Target-zone application of SAP can be advantageous because it reduces the cost of the product to provide SAP only in areas of a product where the SAP is needed, for example, the crotch area of a diaper. Placement of SAP in the area where a liquid insult is expected also decreases the necessity for wicking liquid to a SAP impregnated region. This is an advantage because the requirement for wicking can increase liquid leakage in an absorbent product such as a diaper.

The binder may be sprayed onto the SAP, allowed to dry and the SAP then deagglomerated by, for example, a hammermill or a grinding apparatus. The binder could also be applied to SAP in liquid form as the SAP is sifted onto the target zones, in which case reactivation is not required as the wet binder adheres the SAP in place as it dries.

XI. Binding Examples for Water-soluble Particles

Several examples are provided below to illustrate using binders of the present invention to attach water-soluble particles to southern bleached kraft pulp.

EXAMPLE 12

A 321 gram amount of NB-416 southern bleached kraft fluff obtained from Weyerhaeuser Company (Tacoma, Wash.) may be air-entrained in a blender-like mixing device. 5 grams of glycerin (supplied by Dow Chemicals of Midland, Mich.) may be sprayed onto 288 grams of disodium ethylenediamine tetraacetic acid (EDTA) (supplied by Mallinkrodt Chemical Works of St. Louis, Mo.) and the binder containing particles added and mixed in the device. The blender may be stopped, the product vacuumed out, and spread out in a fume hood to dry overnight. The resulting product under scanning electron microscope examination would have disodium EDTA particles attached to fibers.

EXAMPLE 13

A 321 gram amount of HBA (a crosslinked high bulk fiber available from Weyerhaeuser Company, Tacoma Wash.) may be air-entrained in a blender-like mixing device. 5 grams of glycerin (supplied by Dow Chemical of Midland, Mich.) may be sprayed onto 288 grams of sodium bicarbonate (supplied by J.T. Baker Chemical Co. of Phillipsburg, N.J.) and added and mixed in the device. The blender may be stopped, the product vacuumed out, and spread out in a fume hood to dry overnight. The resulting product would contain fibers with attached sodium bicarbonate particles.

EXAMPLE 14

An NB 416 pulp sheet (southern bleached kraft available from Weyerhaeuser Company of Tacoma, Wash.) may be fed into a hammermill and ground while simultaneously adding binder-coated polyacrylate hydrogel (IM 3900, supplied by Hoechst Celanese of Portsmouth, Va.) and binder-containing ammonium citrate to the mill at rates such that the product contained 54% treated fiber, 42% IM 3900, and 4% ammonium citrate. The binder may be present, for example, as 10% by weight of the product. That mixture may be shunted to an airlay device from M&J Machines (of Horsens, Denmark) and airlaid into a continuous web. The resulting product would include fibers with attached polyacrylate hydrogel and ammonium citrate particles.

EXAMPLE 15

A procedure similar to the one described in Example 13 may be performed using Kitty Hawk (a thermobondable blend of southern bleached kraft and polyethylene fibers available from Weyerhaeuser Company of Tacoma, Wash.). The resulting product may be thermobonded by passing the web through a through-air oven at 140° C. for 0.5 minutes. The resulting thermobonded product would have fibers with attached polyacrylate hydrogel and ammonium citrate particles.

EXAMPLE 16

In this example, sodium oxalate may be bound to the fibers by the. binders of the present invention. A pulp sheet may be prepared as in Example 13. The pulp sheet may be conditioned at 90% relative humidity for 4 hours and then fiberized in a Waring blender. Particles of sodium oxalate with 10% binder may be added to the blender and blending continued. The product would include sodium oxalate in particulate form bound to the cellulose fiber by the glycerin.

EXAMPLE 17

Fibers may be prepared as in Example 15, except with aluminum sulfate (alum) substituted for sodium oxalate. The resulting product would include alum bound to fibers.

EXAMPLE 18

A mixture of binders also may be used to bind particles to the fibers. Fibers may be supplied as in Example 11, but the 5 grams of glycerin may be replaced with a mixture of urea and glycerin. A 40/60 mixture (by weight) of urea and glycerin may be mixed by dissolving urea in the glycerin, and heating the solution to 70–80° C. The heated binder mixture may then be applied to the particles for binding particles to the fibers as in Example 11. The urea/glycerin mixture provides several advantages over the use of glycerin alone. Urea lowers the cost of the binder, while glycerin can soften the fibers. The mixture also provides manufacturing advantages.

In other embodiments urea alone as well as the other binders of the type specified in the foregoing detailed description of the invention and combinations thereof may be used as the binder.

XII. Auxiliary Binder

As previously described, an auxiliary binder or additional binder or binders can be used in addition to the non-polymeric or polymeric binders or combinations thereof in accordance with the present invention. However, the additional binder(s) is selected to not react with the binder or binder combination of the present invention in a manner which prevents this latter binder from having the required functionality. Thus, the preferred auxiliary binders are non-reactive in this way. In addition, polymeric and non-polymeric binders of the invention may be combined with one another and with other binders as long as they do not block the desired functionality.

EXAMPLE 19

A 321 gram amount of a southern bleached kraft fiber (NB-416, supplied by Weyerhaeuser) may be air entrained in a blenderlike mixing device with 212.8 grams of a polyvinylacetate latex (PN-3666H, supplied by H B Fuller of Minneapolis, Minn.). 438 grams of a water swellable polyacrylate hydrogel (Favorsab 800, supplied by Stockhausen of Greensboro, N.C.) may be added to the mixing device. The mixture may then be sprayed with 100 grams of a 50% solution of glycerin (supplied by Dow of Midland, Mich.). The blender may then be stopped and the mixture vacuumed from the blender and placed in a fume hood to air dry overnight. The dried product may then be airlaid into a 6" diameter pad in a laboratory padformer, pressed to a density of approximately 0.077 g/cc, and thermobonded at 140° C. for thirty seconds. The resulting pads are expected to have about 40% bound SAP and improved tensile strength as compared to untreated fluff with SAP and as also compared to binder treated fluff with SAP without the auxiliary binder.

Tensile strength would be highest with polyvinylacetate alone, followed by a combination of polyvinylacetate and glycerin, then glycerin alone. Lowest tensile strength would be with no binder at all.

EXAMPLE 20

Binders of the present invention may be used to bind particles to pulp fibers that contain synthetic thermobonding fibers. In this example, KittyHawk pulp (available from Weyerhaeuser Company) is a mixture of NB316 southern bleached kraft and 22% polyethylene thermoplastic binder fibers. The KittyHawk pulp is used to produce a pulp web, with SAP bound to the fibers as described in Example 3. The web with adhered SAP is then passed through a thermobonder to soften the polyethylene fibers and fuse the fibers of the web to each other to increase web strength.

XIII. Spectroscopic Evaluations

Spectroscopic measurements were made of a binder treated particle made according to the present invention. The results of the NMR and IR studies are presented below.

A. NMR Analysis

EXAMPLE 21

The hydrogen nuclear relaxation time constants shown below were measured by nuclear magnetic resonance spectrometry (NMR), and reflect molecular motion at slow speeds (close to 45 kHz). Both of the glycerin hydrogen signals show relaxation times that decrease with age since glycerin was added to the SAP. This indicates that, with age, glycerin motion keeps slowing down into the 45 kHz range. This motional slowing most likely arises from binding of glycerin into the SAP particles, causing the glycerin molecules to be more tightly held in place. Since neither covalent nor ionic bonding is operative in this composite, the binding would have to be the result of hydrogen bonding involving glycerin and SAP.

Hydrogen Nuclear Relaxation, $T_{1pH}$, at 45 kHz

Sample: IM 3900 with ca. 15% glycerin.

Aging is at ambient conditions.

| | $T_{1\rho H}$, msec (std. devn.) | |
|---|---|---|
| Age, days | —OH, H$_2$O Peak | —CH$_2$—, —CH— Peak |
| 0 | 34 (11) | 30 (6) |
| 11 | 10.4 (0.5) | 9.3 (0.4) |
| 17 | 6.0 (0.4) | 5.3 (0.5) |
| 28 | 2.6 (0.2) | 2.3 (0.1) |

XIV. Activation

The binders of the present invention have the advantage of being activatable from an inactive state on the particles by addition of liquid, heating or by kinetic energy such as supply by mechanical agitation. Hence, a liquid binder can be applied to particles in the absence of the fibers to be bound. The binder is then dried or allowed to dry, for example until the binder and particles reach an equilibrium moisture content with ambient air. Alternatively, the binder can be combined with particles as a solid. At a later stage of processing, heat, kinetic energy, pressure, or a liquid such as water is added to the particles resulting in an activation of the binder. The particulates may then be added to the fibers, and the binder secures the particulates to the fibers. This subsequent processing of the fibers to attach the particles can occur, for example, at a separate location from the location where the fibers are produced. Therefore, manufacturers of products can add particulates of interest (e.g., superabsorbent particles or fibers; antimicrobial particles, etc.) at the place of manufacture of the end products that incorporate the particles. Also, more than one type of particulate material (including water soluble and water insoluble particles) may be added, if desired. Particles without the required functionality would not be bound in the same manner.

It also has been found that some of the binders of the present invention can be reactivated by mechanical agitation (the application of kinetic energy). For example, glycerin binder may be applied to particles such as SAP. The glycerin binder may be allowed to dry overnight, and the binder-containing particles may be mixed with fibers and then mechanically agitated to reactivate the glycerin binder and bind the particles to the fibers. Mechanical agitation may take place, for example, in a defiberizer where a sheet or mat of fibers are defiberized while being intimately mixed with the binder containing SAP. Hence, the binder may be activated by providing heat, an activating fluid, or by applying kinetic energy to the particles, or to the fibers in the presence of the particles, (or by adding the particles to the fibers while activating fluid is on the fibers.)

XV. Binder Activation Examples

Binder activation in the present invention allows binder to be added to particles before the particles are added to the fibers. The binder is subsequently activated by addition of liquid, heat, or by kinetic energy such as resulting from agitation, and particles are bound to the fibers. The binder containing particles may be added to the fibers either before binder activation, after binder activation, or simultaneous with activation. If binder containing SAP and/or other particles are to be added to cellulose fibers, for example, the binder containing particles may be applied to a pulp sheet which is subsequently fiberized. An activation liquid such as water may be added to the pulp before or after fiberization, and the binder containing particles may be added before or after water addition, or simultaneously with the water. If binder containing SAP or other particles are added after water addition, the particles should be applied to the fibers prior to complete evaporation of the added water from the fibers. Water can also be added as an activation liquid in other ways, such as by very humid air, a fog or mist, or as steam.

Activation can be of all the fibers, or only portions of the fibers, such as target zones or portions of the mat where particulate binding is desired. The particles may be added to the mat and adhered to the target zones of the mat upon activation. In some embodiments, the binder is applied as a solid and heated during a later processing stage to activate the binder by softening it such that it binds the particles to the fibers. The particles may be added in a pattern corresponding to a desired distribution (for example a non-homogeneous distribution) of particles in the fibrous material. Most commonly, however, activation is accomplished by using a binder solvent to moisten the binder on the particles for application to a targeted area of the product.

In yet other embodiments, the binder is applied to the particles and then activated by applying kinetic energy to the binder containing particles and fibers. Neat polypropylene glycol (MW 2000) binder, for example, may be sprayed on particles and allowed to air dry. These particles are then added to the fibers as the fibers are mechanically agitated in a blender or defiberizer to kinetically activate the binder and bind the particles to the fibers. For kinetic activation, the binder may be added as a liquid or a solid to the particles. In the case of liquid addition, the liquid is allowed to air dry, and then reactivated by mechanically agitating the fibers and binder.

Activation of the binder may be performed prior to adding the particles, subsequent to adding the particles, or simultaneously with addition of the particles. Once the binder is activated, it adheres a substantial portion of the particles to the fibers, wherein "a substantial portion" refers to about half of the particles added. Of the particles that are adhered, at least half of them (and more typically substantially all of them, e.g., over 90%) are adhered to the binder by non-covalent bonds, namely hydrogen bonds or coordinate covalent bonds, and the binder is in turn adhered to the fibers by hydrogen bonds.

The activating step may be performed after the curing step is complete, if a curing step is to be performed.

The following example will illustrate several specific applications of the activation process, and are not intended to limit the invention to the disclosed methods.

EXAMPLE 22

0.30 grams of urea (supplied by Aldrich, Milwaukee, Wisc.) were dissolved in a mixture of 9 milliliters of ethanol and 1 milliliter of deionized water. 1.0 milliliter of that solution was dropped onto 30 grams of a starch graft polyacrylate hydrogel (IM 3900; supplied by Hoechst Celanese, Portsmouth, Va.) and the resulting mixture was air entrained in blender-like mixing device for 30 seconds to ensure complete mixing. The mixture was then allowed to air dry for two weeks. 1.2 grams of a southern bleached kraft pulp sheet (NB 416; supplied by Weyerhaeuser, Tacoma Wash.) were fiberized in a Waring blender. While the blender was running, 0.80 grams of the urea-treated hydrogel were added to the fluff. The blender was then stopped and the mixture was removed. The resulting product was examined by light microscopy and revealed no fibers with attached hydrogel particles. However, an 18.5 gram sample of the urea-treated hydrogel was air-entrained in a blender-like mixing device and mixed with 0.51 grams of distilled water. Attached particles were formed when 0.80 grams of the water-activated urea-treated hydrogel were blended with 1.2 grams of fluff fibers.

EXAMPLE 23

0.30 grams of para-aminosaliciylic acid (supplied by J. T. Baker, Phillipsburg, N.J.) were dissolved in a mixture of 9 milliliters of ethanol and 1 milliliter of deionized water. 1.0 milliliter of that solution was dropped onto 30 grams of a starch graft polyacrylate hydrogel (IM 3900, supplied by Hoechst Celanese, Portsmouth, Va.) and the resulting mixture was air-entrained in a blender-like mixing device for 30 seconds to ensure complete mixing. The mixture was then allowed to air dry for two weeks. 1.2 grams of a southern bleached kraft pulp sheet (NB 416; supplied by Weyerhaeuser, Tacoma Wash.) were fiberized in a Waring blender. While the blender was running, 0.80 grams of the para-aminosaliciylic acid-treated hydrogel were added to the fluff. The blender was then stopped and the mixture was removed. The resulting product was examined by light microscopy and revealed no fibers with attached hydrogel particles. However, fibers with attached particles were formed when a 1.2 gram sample of the pulp sheet had been conditioned in a 90% relative humidity environment for two hours before blending with the binder-treated hydrogel.

EXAMPLE 24

30-gram samples of a starch graft polyacrylate hydrogel (IM 3900; supplied by Hoechst Celanese, Portsmouth, Va.) were treated with either glycine, taurine, or ammonium citrate in a manner similar to that described above in Example 23. While some adjustments in the volumes of solvents used were necessary to effect dissolution of the binders, binder add-on levels were held constant and attachment attempts yielded similar results.

XVI. Thermoplastic Binders

An auxiliary binder also may be used to help bind fibers to each other above the melting point of the auxiliary binder. The auxiliary binder may be a solid thermoplastic material that is applied to the fibers and softened by elevating the temperature during the binding step to above the softening temperature of the auxiliary binder. The auxiliary binder is thereby temporarily softened, rendered more fluid (which for purposes of convenience may be referred to as auxiliary binder melting) and subsequently resolidified as the temperature cools, which thermoplastically binds the fibers to each other, and the particles to the fibers. The auxiliary binder may also contain a hydrogen bonding functionality that hydrogen bonds the particles to the fiber. Examples of auxiliary binders that are thermoplastic and also contain hydrogen bonding groups include ethylene vinyl alcohol, polyvinyl acetate, acrylates, polycarbonates, polyesters and polyamides. Further information about the use of such auxiliary binders can be found in U.S. Pat. No. 5,057,166.

The auxiliary or second binder can be added to the fibers, either before or after particles containing a first binder, to help bind the fibers to each other and provide additional binding between the fibers and particles. A suitable second binder would be a thermoplastic or thermosetting binder. In the case of thermoplastic polymers, the polymers may be a material which remains permanently thermoplastic. Alternatively, such polymers may be a material which is partially or fully crosslinkable, with or without an external catalyst, into a thermosetting type polymer. As a few specific examples, suitable thermoplastic binders can be made of the following materials: ethylene vinyl alcohol, polyvinyl acetate, acrylic, polyvinyl acetate acrylate, acrylates, polyvinyl dichloride, ethylene vinyl acetate, ethylene vinyl chloride, polyvinyl chloride, styrene, styrene acrylate, styrene/butadiene, styrene/acrylonitrile, butadiene/acrylonitrile, acrylonitrile/butadiene/styrene, ethylene acrylic acid, polyethylene, urethanes, polycarbonate, oxide, polypropylene, polyesters, and polyimides.

In addition, a few specific examples of thermoset binders include those made of the following materials: epoxy, phenolic, bismaleimide, polyimide, melamine/formaldehyde, polyester, urethanes, urea, and urea/formaldehyde.

More than one of these materials may be used to treat the fibers. For example, a first coating or sheath of a thermoset material may be used followed by a second coating of a thermoplastic material. The binder containing superabsorbent particles or other particles are then typically adhered to the outer binder material which should have the functionality as explained above. During subsequent use of the fibers to make products, the thermoplastic material may be heated to its softening or tack temperature without raising the thermoset material to its curing temperature. The remaining thermoset material permits subsequent heating of the fibers to cure the thermoset material during further processing. Alternatively, the thermoset material may be cured at the same time the thermoplastic material is heated by heating the fibers to the curing temperature of the thermoset with the thermoplastic material also being heated to its tack temperature.

Certain types of binders enhance the fire resistance of the treated fibers, and thereby products made from these fibers. For example, polyvinyl chloride, polyvinyl dichloride, ethylene vinyl chloride and phenolic are fire retardant.

Surfactants also may be included in the auxiliary binder as desired. Other materials may also be mixed with the auxiliary binder to impart desired characteristics to the fibers. For example, particulate material, such as pigments, also may be included in the auxiliary binder for application to the fibers.

EXAMPLE 25

As previously described, an auxiliary binder can be used in addition to the polymeric binders of the present invention. A 3210 gram amount of southern bleached kraft binder (NB-416, supplied by Weyerhaeuser Company) may be air entrained in a blenderlike mixing device and sprayed with 2128 grams of a polyvinyl acetate latex (PN-3666H, supplied by H. B. Fuller of Minneapolis, Minn.). While still mixing, 4073 grams of a water-swellable polyacrylate hydrogel (IM 1000–60, supplied by Hoechst-Celanese of Portsmouth, Va.) with 580 grams of polypropylene glycol (supplied by Union Carbide of Danbury, Conn.) may be added. The blender may be kept running and the mixture shunted into a flash tube dryer. The dried product may then be airlaid, for example, as a 16 inch wide web on a Danweb airlay machine, pressed to a density of approximately 0.15 g/cc, and thermobonded at 140° C. for thirty seconds. The resulting web would have 40% bound SAP and improved tensile strength (as compared to untreated fluff with SAP).

XVII. Application of Binder

The binders of the present invention can be added to the particles in any convenient manner. One such procedure is to spray the binder or binders on to the particles as the particles are conveyed past a sprayer on a conveyor belt or as the particles fall through air, for example toward a web of fibers. The particles may also be slurried with or immersed in binder. In this case, the particles would typically be milled to break up agglomerations. For solid binders, blending of the particles and binder may be accomplished or the binder may simply be sprinkled onto or otherwise comingled with the particles, followed by a fixation step such as addition of heat or liquid. These particles can, while still wet in the case of a liquid binder or following reactivation of a liquid or solid, be combined with the fibers.

The particles can also be allowed to dry for later reactivation with a reactivation fluid, such as a reactivation liquid and combined with the fibers at that time. An example of when it may be desirable to apply the binder to the particles and thereafter activate the binder in the presence of fibers is when the particles are added to fibers at a remote site from the site where the fibers are produced. The remote or second location may be, for example, a location where a manufacturer combines fibers and particles into articles, such as absorbent articles. Particles may be added from conventional volumetric feeders in a hammermill or from injectors on a paper making line.

The invention is not limited to any specific mechanism for combining the binder and particles.

XVIII. Production of High Bulk Fibers

Production of high bulk fibers with intrafiber crosslinks is known in the art. Processes for making such fibers are described in EP 440 472 A1; EP 427 317 A2; EP 427 316 A2; and EP 429 112 A2, as well as U.S. patent application Ser. No. 07/607,268 filed Oct. 31, 1990, and its published European counterpart. These high bulk fibers may be used in the present invention, with particles bound to them by the binders disclosed herein. Since methods of making high bulk fibers are known, only a brief description of one such process is given below.

A. Overall System

The apparatus 110 (FIG. 3) comprises a conveying device 112 for transporting a mat 114 of cellulose fibers or other fibers through a fiber treatment zone 116; an applicator 118 for applying a treatment substance such as a crosslinking substance from a source 119 thereof to the mat 114 at the fiber treatment zone 116; a fiberizer 120 for completely separating the individual cellulose fibers comprising the mat 114 to form a fiber output comprised of substantially unbroken cellulose fibers substantially without nits or knots; and a dryer 122 coupled to the fiberizer for flash evaporating residual moisture from the fiber output and for curing the crosslinking substance, thereby forming dried and cured cellulose fibers.

The mat 114 of cellulose fibers is preferably in an extended sheet form stored in the form of a roll 124 until use. It is normally not necessary that the cellulose fibers comprising the mat 114 be completely dry. Since cellulose is a hydrophilic substance, molecules thereof will typically have a certain level of residual moisture, even after air drying. The level of residual moisture is generally 10% wt/wt or less, which is not detectable as "wetness." FIG. 3 also shows that more than one supply, such as multiple rolls 124, of the mat 114 of cellulosic fibers can be simultaneously processed using the present invention.

At the fiber treatment zone 116, sprayers or other applicators 118 apply chemicals such as crosslinking agents to the mat. Typically chemicals are applied uniformly to both sides of the mat. The wetted mat passes between a pair of rollers 128 which assist in distributing the chemicals uniformly through the mat. Other applicators may also, of course, be used.

The crosslinking substance is a liquid solution of any of a variety of crosslinking solutes known in the art. If required, the crosslinking substance can include a catalyst to accelerate the bonding reactions between molecules of the crosslinking substance and cellulose molecules. However, many if not most crosslinking substances do not require a catalyst.

Preferred types of crosslinking substances are selected from a group consisting of urea derivatives such as methylolated urea, methylolated cyclic ureas, methylolated lower alkyl substituted cyclic ureas, methylolated dihydroxy cyclic ureas, and mixtures thereof. A specifically preferred crosslinking substance would be dimethyloldihydroxyethylene urea (DMDHEU). In addition, crosslinking substances can be polycarboxylic acids, such as citric acid. Crosslinking materials are known in the art, such as described in the previously mentioned Chung patent, U.S. Pat. No. 4,935,022 to Lash, et al., U.S. Pat. No. 4,889,595 to Herron, et al., U.S. Pat. No. 3,819,470 to Shaw, et al., U.S. Pat. No. 3,658,613 to Steijer, al., U.S. Pat. No. 4,822,453 to Dean, et al., and U.S. Pat. No. 4,853,086 to Graef, et al.

Suitable catalysts include acidic salts which can be useful when urea-based crosslinking substances are used. Such salts include ammonium chloride, ammonium sulfate, aluminum chloride, magnesium chloride, or mixtures of these or other similar compounds. Alkali metal salts of phosphorus-containing acids may also be used.

In FIG. 3, the crosslinking substance applied to the mat 114 is obtained from a supply 119 thereof, such as a tank or analogous vessel.

Crosslinked cellulose fibers are individual fibers each comprised of multiple cellulose molecules where at least a portion of the hydroxyl groups on the cellulose molecules have been covalently bonded to hydroxyl groups on neighboring cellulose molecules in the same fiber via crosslinking reactions with extraneously added chemical reagents termed "crosslinking substances" or "crosslinking agents." Suitable crosslinking agents are generally of the bifunctional type which create covalently bonded "bridges" between said neighboring hydroxyl groups.

B. Conveying Device

Referring further to FIG. 3, each mat 114 of cellulosic fibers is conveyed by a conveying device 112, which carries the mats through the fiber treatment zone 116. FIG. 3 also shows a further portion of one type of conveying device comprised of a first pair of rollers 126 and a second pair of rollers 128 for each mat 114. The first and second pair of rollers 126, 128 are particularly effective for urging the corresponding mat at a substantially constant and controlled rate of speed.

C. Fiber Treatment Zone

Each mat 114 is urged by the first and second pair of rollers 126, 128 through the fiber treatment zone 116 where the mat 114 is impregnated with a liquid crosslinking substance. The crosslinking substance is preferably applied to one or both surfaces of the mat using any of a variety of methods known in the art useful for such a purpose, such as spraying, rolling, dipping, or analogous method. Combinations of spray and roller applicators can also be employed.

The crosslinking substance is typically applied in an amount ranging from about 2 kg to about 200 kg chemical per ton of cellulose fiber and preferably about 20 kg to about 100 kg chemical per ton of cellulose fiber.

D. Fiberizer

The next subsystem following the fiber treatment zone is a fiberizer 120 which serves to comminute one or more mats 130 impregnated with the crosslinking substance into individual substantially unbroken cellulose fibers comprising a fiber output.

Referring further to FIG. 3, a first conveyer fan 260 of conventional design can be utilized for propelling the fibers from the outlet 162 of the attrition device 132 through a conduit 262.

An optional component of the fiberizer 120 is a first cyclone 264 or similar apparatus known in the art, utilized in a conventional manner to concentrate the fibers passing out of the outlet 162 of the attrition device 132. The first cyclone 264 receives the fibers through the conduit 262 coupled thereto.

Excess air can be recovered at the top 266 of the first cyclone 264 and recycled as required through a conduit 268 to a location upstream of the first conveyer fan 260 (if used). Such additional air can be beneficial for easing the transfer of the fibers through the first conveyor fan 260.

A disk refiner 268 is another optional component of the fiberizer 120 which can be employed to effect additional separation of fibers (removal of knots) if required. The disk refiner 268 is of a type known in the art and comprises a disk refiner inlet 270 and a disk refiner outlet 272. A representative disk refiner 268 is type DM36 manufactured by Sprout-Bauer, Incorporated of Muncie, Pa. If the disk refiner 268 is used, the inlet 270 thereof is coupled via a conduit 274 to an outlet 276 of the first cyclone 264.

A second conveyor fan 278 may optionally be utilized to urge propagation of the fibers through a conduit 180 downstream of the disk refiner 268. Excess air can be recovered from the top 266 of the first cyclone 264 and routed via a conduit 281 to a tee 282 just upstream of the second conveyor fan 278.

Another optional component of the fiberizer 120 is a fluff generator 290 which receives the fibers from the optional second conveyor fan 278 through a conduit 284. The fluff generator is described in detail below and in copending U.S. Patent application Ser. No. 07/607,157.

E. Dryer

Referring further to FIG. 3, a preferred embodiment of the present apparatus 110 includes a dryer 122 which is utilized to perform two sequential functions: remove residual moisture from the fibers and cure the crosslinking agent. Preferably, the dryer 122 comprises a drying zone 373 for receiving fibers, e.g. from fluff generator outlet 304 and for removing residual moisture from the fibers via a "flash drying" method and a second drying zone 360, 362 for curing the crosslinking agent. In FIG. 3, the curing starts in zone 360 and continues through zone 362.

The FIG. 3 embodiment shows that zone 373 is coupled to the fluff generator outlet by a conduit 372 and to a source 374 of heated air, typically produced by combustion of a supply of natural gas 376 and fresh air 378. The temperature of heated air is regulated to maintain the temperature of the drying zone 373 within a range of about 200° C. to about 315° C. As the fiber output passes into the drying zone 373, the wet fibers comprising the fiber output are substantially instantaneously exposed to the high temperature in this zone. Such rapid exposure to high temperature imparts a "flash drying" effect to the fibers, thereby causing rapid and thorough drying and separation of the fibers. The passage time through the drying zone 373 is preferably less than one second.

The FIG. 3 embodiment shows that the first zone 360 is comprised of a first tower 364 comprised of a body portion 366, an inlet 368, and a first tower outlet 370. The dryer zone 373 is coupled via a conduit 372 to the outlet of the fluff generator 290.

In FIG. 3, the first tower 364 is shown preferably coupled via a conduit 380 to a down tube 382, which is coupled via a conduit 384 to a third conveyor fan 386 located at an inlet 388 of a second tower 390. The third conveyor fan 386 transports the fibers through the dryer which thereby pass into the second tower 390. As the fibers are lofted through the second tower 390, they are still exposed to a curing temperature within a range of about 140° C. to about 180° C., which is sufficient to effect curing of the crosslinking agent without scorching the dry fibers. The lofting keeps the fibers separated until the crosslinking reaction is complete. The curing temperature depends upon the type of crosslinking material used to treat the fibers and also is set at a level so as to not scorch the fibers during curing. It should be noted that single stage dryers may also be used.

The dried and cured fibers exiting the dryer outlet of tower 390 have an extremely low level of nits and virtually no knots. Further, they are not discolored from scorching and the like, and have a median fiber length substantially unchanged from the median length of the fibers comprising the mat 14.

FIG. 3 also shows a second cyclone 400 of conventional design coupled. via a conduit 402 to the outlet of tower 390, serving to concentrate the fibers passing therethrough in preparation for collection. The resulting concentrated fibers can be collected using any of a number of collection devices 408 known in the art, such as fiber bagging devices.

EXAMPLE 26

Theoretical

In this example, non-woven fibrous mats were impregnated with a crosslinking agent, fiberized, dried, and cured using the apparatus as diagrammed schematically in FIG. 3.

Two 52-inch-wide mats of southern pine kraft wood pulp fibers (type NB316 from Weyerhaeuser Company) and having a basis weight of 680 g/m$^2$ were fed to the apparatus. The mats were impregnated using dimethyloldihydroxyethylene urea at a concentration of about 5%, applied over both sides of each mat using a combination of spray nozzles and impregnation rollers. The loading level of crosslinking agent was about 4.5% w/w.

The treated fiber mats were fed at the rate of 8 meters/min to the attrition device 32. The specific attrition device used in this example was equipped with six mat inlets and a rotor having 16 rows of hammers as described above around the circumference of the rotor. The rotor had a diameter of 30 inches and was rotated at an angular velocity of 1200 rpm by an electric motor. Other rpm rates have also been tested and have proven satisfactory, including extremely high rpm rates.

Random samples of fibers were obtained from the output attrition device and observed for nits. These samples were 2.6 grams and were consistently observed to have fewer than three nits on the average with most samples having no nits. The attrition device was flushed with water once every sixteen hours for cleaning purposes.

A disk refiner was employed downstream of the attrition device. This specific disk refiner was a DM36 refiner as previously mentioned. A fluff generator as described in FIGS. 7–9 was also employed in this downstream of the disk refiner. The temperature at the dryer input in this example was within the range of 200° C. to 315° C. The temperature at the second tower outlet was within the range of 140° C. to 180° C. Crosslinked fiber at the output of the dryer was produced at a rate of about 5000 pounds per hour. The particle binders and particles of the present invention can be added before, after, or simultaneously with curing. The term "curing in the presence of the binder" means that the binder containing particles may be added before or simultaneously with curing. Curing in the presence of the binder is not usually a problem because the binder cannot participate in the intrafiber crosslinking reaction, and the binder would not be affected by the curing step. In certain situations, however, the binder on the particles may also form covalent intrafiber crosslinks. Polycarboxylic acids (such as citric acid), polyols (such as propylene. glycol) and polyamines (such as ethylene diamine) may function as crosslinking agents, and may be consumed during the curing step in the formation of covalent crosslinks. Hence in the limited case in which the binder material on the particles is also a crosslinking agent, steps should be taken to prevent the binder from being consumed as a crosslinker in the curing step. When the crosslinking material is not cured in the presence of the binder, that is when the binder containing particles are added after curing, no steps need be taken to inhibit covalent bond formation.

XIX. Composite Absorbent Product

In accordance with the present invention, absorbent structures or articles may be made from the fibers, with binder and adhered particulates. These articles may be composite structures (e.g., made of plural materials). For example, the articles may have a core of plural types of fibers, or fiber layers, with or without covering materials. These products are capable of absorbing significant quantities of water and other fluids, such as urine and other body fluids. Such products include, but are not limited to, disposable diapers, sanitary napkins, incontinent pads, towels and the like.

Figure 4:
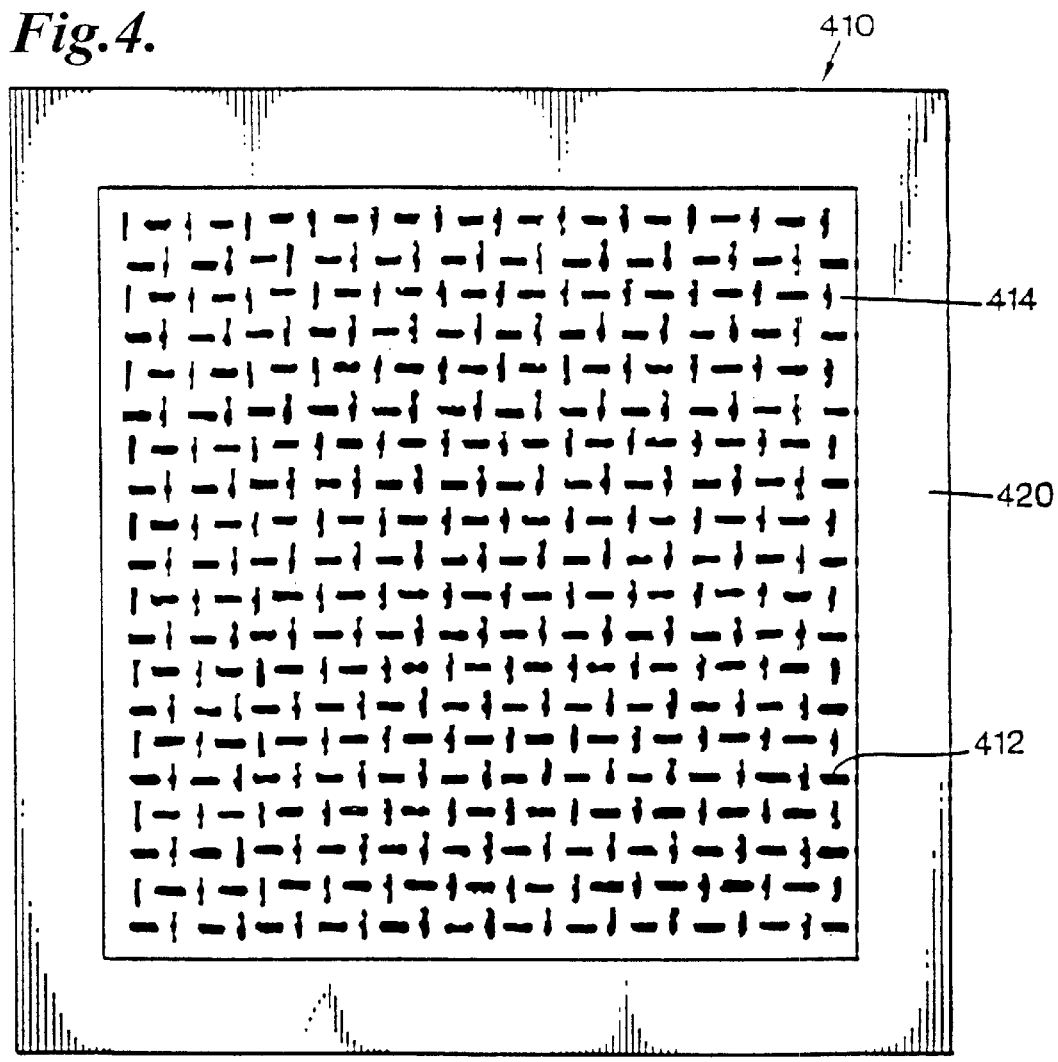
FIG. 4 is a top plan view of a structure into which particles with binders are combined with fibers, the fibers being in the form of an illustrated absorbent pad.
Figure 5:
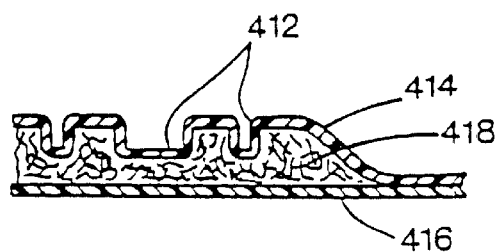
FIG. 5 represents a partial sectional view of the pad of FIG. 4.

FIGS. 4–5 illustrate an absorbent pad structure which may be formed from fibers of the present invention, whether or not they are blended with other fibers. FIGS. 4 and 5 represent an absorbent pad 410 having a heat embossed screen pattern 412. Pads having no pattern may also be used. A pad having a cover sheet 414 and a backing sheet 416 may be formed, for example, by placing a square fiber piece cut from the sheet onto a corresponding precut backing sheet. A corresponding precut cover sheet is placed over the top of the fiber 418 on the backing sheet. This assembly may then be adhesively bonded around a continuous margin 420.

With reference to FIGS. 6–7, an absorbent structure in the form of a bandage is shown. A bandage 430 for application to a wound to absorb blood and other bodily fluids is shown. An absorbent pad 440 is securely mounted to an exterior or pad mounting surface 434 of a backing strip 436. Fibers 441 are contained in pad 440, and particles are attached to the fibers 441 in accordance with the present invention. Any suitable mounting or securing means may be used to affix pad 440 to the surface 434 of the strip 436. However, it is preferable for surface 434 to be coated with an adhesive so that the pad 440 may be adhesively mounted in place. An exemplary adhesive is ethylene vinyl acetate adhesive. It is also desirable for the overall surface 438 of backing strip 436 to be coated with a conventional adhesive. Surface 438 is the surface which is affixed to the area of the skin surrounding the wound. Conventional "peel-back" tabs may be used to protect the adhesive coating and pad 440 until the bandage is to be applied. This type of backing strip is well known in the art.

The backing strip 436 may be of any known flexible material suitable for application to the skin. It is preferable for the strip 416 to be of a material which is impermeable to the passage of liquid so that fluid from a wound is contained by the bandage. However, the strip 436 may be apertured or otherwise breathable to permit air to reach the wound to promote the healing process. A specific example of a suitable backing strip 436 is a polyethylene film.

As in the other structures described, a variety of combinations of antimicrobials and other particles may be used in the fibers 441 of such a bandage. Again, however, the particles are adhered securely in place when the particles have a hydrogen bonding or a coordinate covalent bonding functionality, the fibers to which these particles are bound have a hydrogen bonding functionality, and wherein the binder is selected from the group consisting of a polypropylene glycol, a polypropylene glycol/polyethylene glycol copolymer, a polycarboxylic acid, such as polyacrylic acid, a poly(lactone) polyol, such as poly(caprolactone) diol, a polyamide, a polyamine, a polysulfonic acid, and combinations thereof, and the polymeric binder has a hydrogen bonding or a coordinate covalent bond forming functionality on each repeating unit of the binder. Nonpolymeric binders would include organic binders such as glycerin, a glycerin monoester, a glycerin diester, ascorbic acid, urea, glycine, pentaerythritol, a monosaccharide or a disaccharide, citric acid, tartaric acid, taurine, dipropylene glycol, and urea derivatives such as DMDHEU. Suitable saccharides include glucose, sucrose, lactose, ribose, fructose, mannose, arabinose, and erythrose. Two different particles, such as antimicrobials in particulate form, may be adhered to the same fiber. In the alternative, each different type of antimicrobial particle or other particle may be adhered separately to different fibers. Also, blends of fibers may be included in absorbent structures such as pad 366. For example, these blends may include fibers with adhered antimicrobial (one or more antimicrobials) particles and adhered superabsorbent particles; fibers with one or more antimicrobial particles without superabsorbent particles blended with fibers having adhered superabsorbent particles with or without antimicrobial particles; and combinations of such fibers with untreated fibers and/or binder coated fibers without superabsorbent particles or antimicrobial particles. In addition, other particles, such as anticoagulants or hemostatics may be attached to the fibers.

The absorbent pad of bandage 430 may also include a cover sheet that is typically made of any suitable material which will readily permit the passage of liquid through the cover sheet to the fibers 441, such as nonwoven fiber webs of fibers such as, for example, rayon, nylon, polyester, propylene and blends thereof. One specifically preferred cover sheet material is a 70 percent rayon/30 percent polyester blend having a basis weight of 18 $g/m^2$ from Scott Paper Company.

Figure 8:
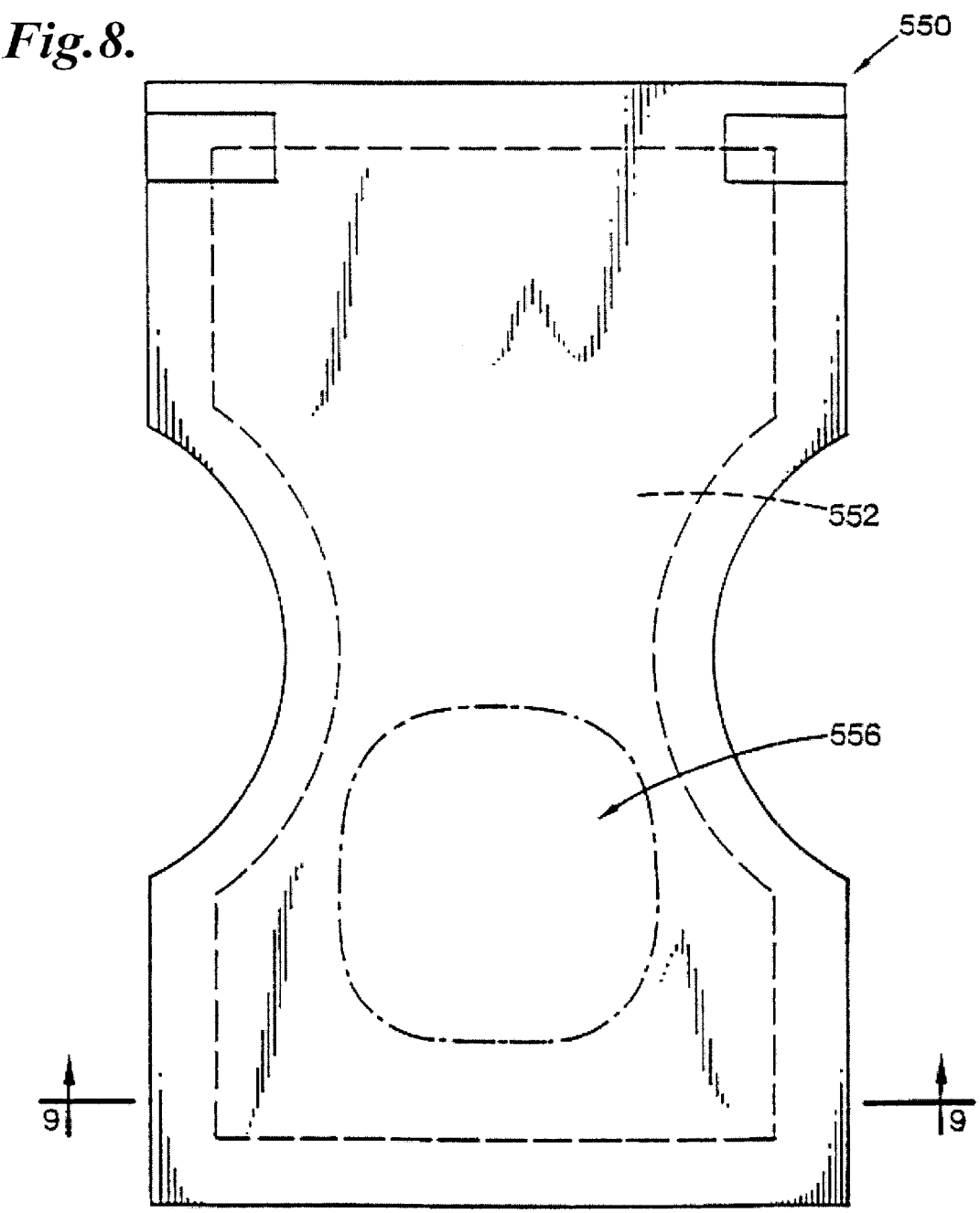
FIG. 8 is a plan view of a disposable diaper including a core of particles with binder adhered to fibers in accordance with the present invention.
Figure 9:
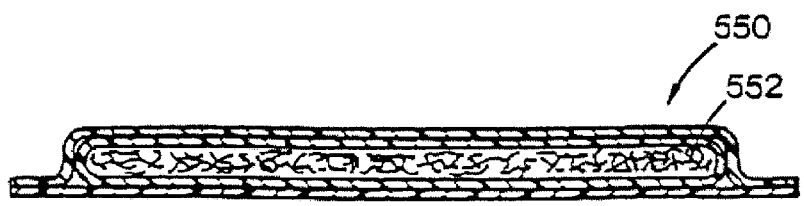
FIG. 9 is a vertical sectional view along line 9—9 of the diaper of FIG. 8.

FIGS. 8 and 9 illustrate a conventional disposable diaper 550 with a core 552 which is comprised of fibers of the present invention with adhered superabsorbent particulate materials. These particulate materials may be confined to a target zone (for example, the front or crotch portion of a diaper indicated at 556) or of a heavier concentration in the target zone. This can be accomplished by airlaying fibers of the present invention in such a zone. Also, the core may be reactivated by melting the binder or moistening the target zone with water. The superabsorbent particles may be sprinkled on or otherwise applied to this wetted zone. As the zone dries, the particles are adhered in place.

XX. Densification

The products such as described above, as well as webs of the fibers of the present invention, can also be densified by external application of pressure to the web. The web could be densified by passing it through a set of calendar rolls set at 60 and 90 pli (pounds per linear inch, as in a calendar press) respectively to yield sheets with increased densities. Densification may alternatively be provided by compaction rolls or presses. Densification is preferably performed to produce a product that has a density of about 0.05 to 0.7 g/cc, more preferably 0.1 to 0.3 g/cc.

An example of densification using some of the binders of the present invention is given below:

EXAMPLE 27

Any of the products of the present invention can be formed into 550 gram/square meter sheets, six inches in diameter, in a laboratory padformer. Those pads may then be passed through a set of calendar rolls set at 60 and 90 pli, respectively to yield sheets with densities of 0.3 and 0.5 g/cc.

EXAMPLE 28

A 5 gram amount of polypropylene glycol is diluted with 5 grams deionized water. The resulting solution is sprayed on 438 grams of IM 1000F (supplied by Hoechst-Celanese, of Portsmouth, Va.). The binder containing particles are then added to 321 grams of an intrafiber crosslinked cellulose fluff (HBA from Weyerhaeuser Company of Tacoma, Wash.) that was air entrained in a blender like mixing device. The resultant mixture may then be vacuumed from the blender and spread on a counter to dry overnight. Then 550 gram/ square meter handsheets, six inches in diameter, can be made in a laboratory padformer. Those pads may then be pressed at 2000 and 3000 psi (or 60 and 90 pli in a calendar roll), respectively, to yield densified sheets.

XXI. Particulate Binding

Figure 10:
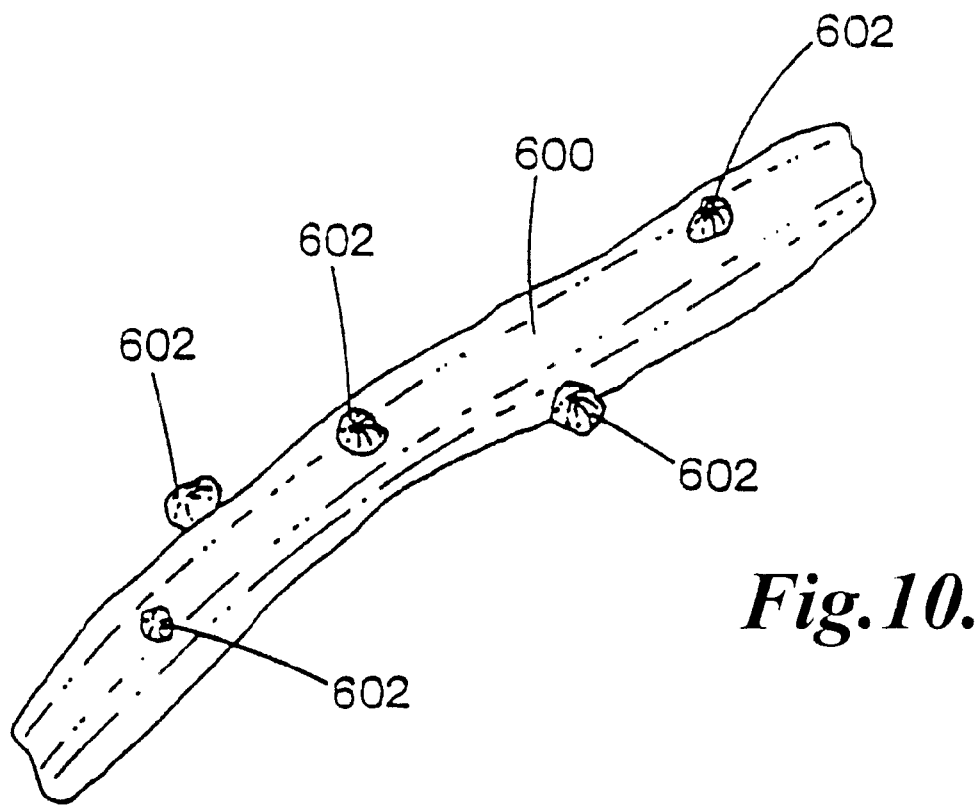
FIG. 10 is a view of an enlarged fiber with particles bonded to the fiber with the binders of the present invention.

FIG. 10 illustrates an isolated, enlarged cellulose fiber 600 with SAP particles 602 bound to it by a binder of the present invention. This drawing illustrates an example of the SAP retaining its discrete particulate form following binding to the fibers. Some particle to particle fusion may occur in accordance with this invention, but maintenance of a discrete particulate form excludes formation of a completely confluent film in which the particles lose their particulate identity. Such a confluent film produces gel blocking that interferes with efficient liquid absorption into the fibers.

The shown fiber 600 iselongated, and has an aspect ratio (ratio of length to width) of about 10:1 to 5:1, preferably about 10:1.

Figure 11:
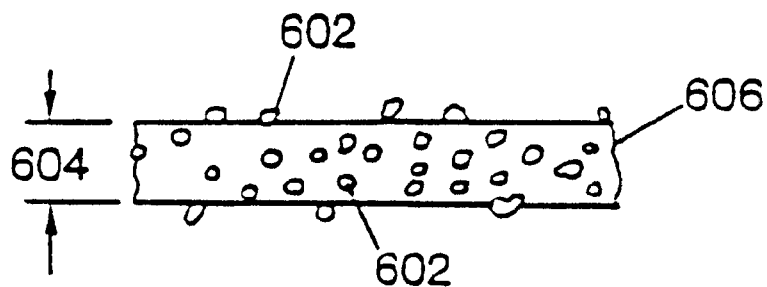
FIG. 11 is a schematic view of a cellulose mat with particles bound to all its surfaces and throughout its depth.
Figure 12A:
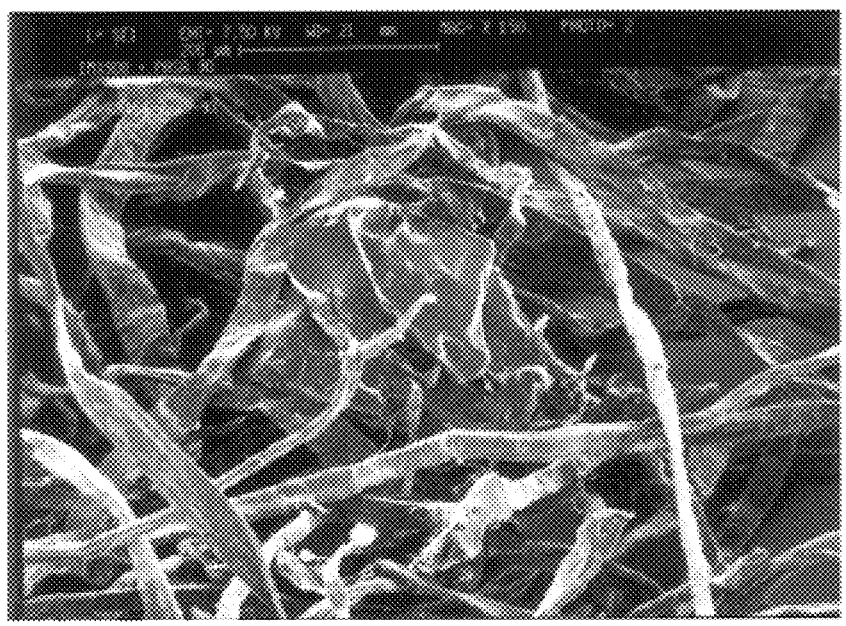
FIG. 12A, 12B are photomicrographs of particles adhered to fibers with a para-aminosalicylic acid binder.
Figure 12B:
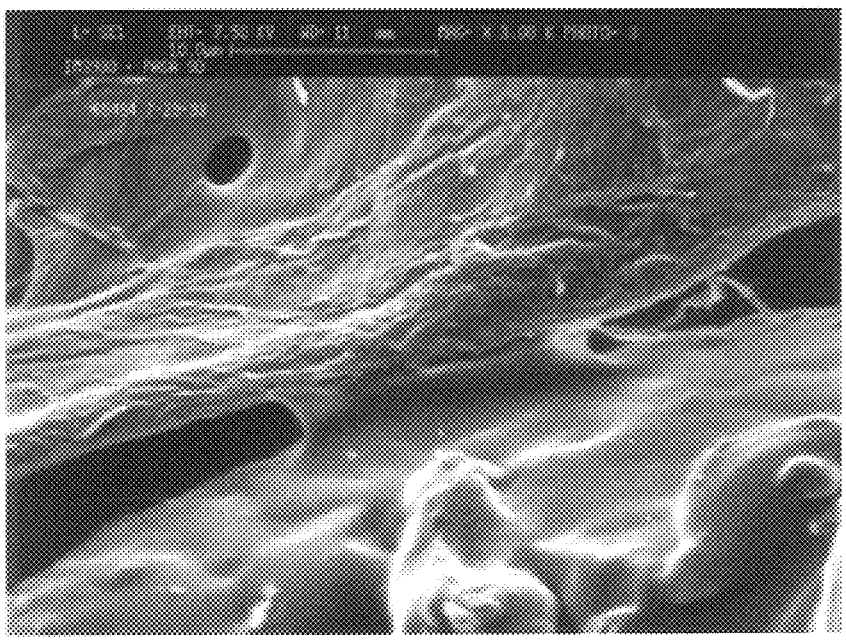
Figure 13A:
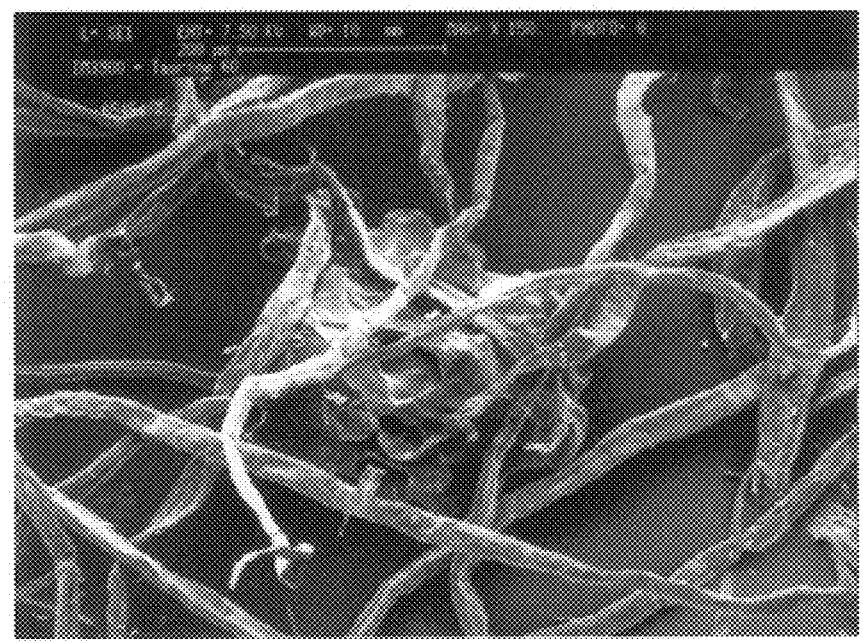
FIGS. 13A, 13B are photomicrographs of particles bound to fibers with a taurine binder.
Figure 13B:
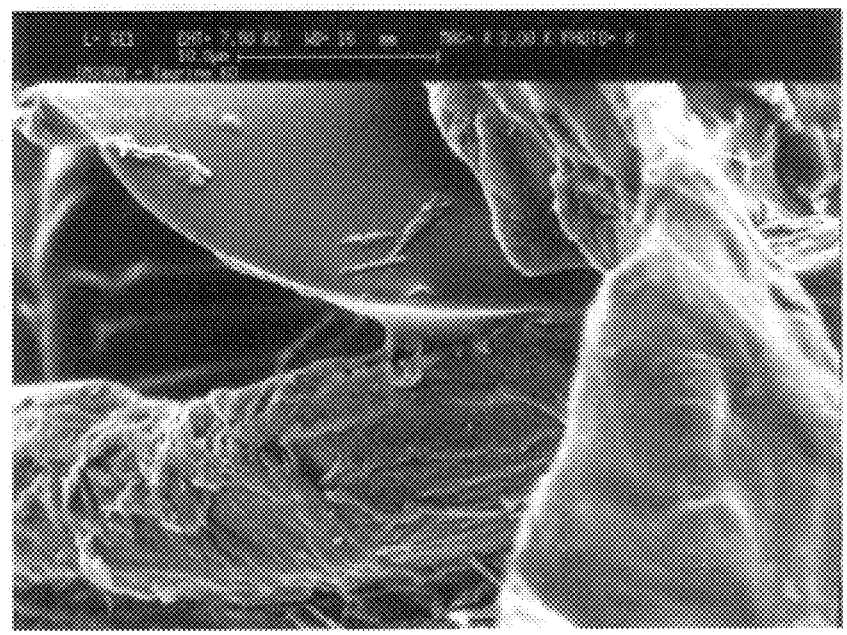

FIG. 11 shows the particles 602 distributed substantially uniformly throughout the depth 604 of a pad 606. The particles are also shown adhering to all the surfaces of the pad. Particles may be distributed in any desired pattern throughout the pad in accordance with this invention, and need not necessarily adhere to all surfaces or be distributed throughout the volume of the mat, or distributed uniformly.

As can be seen from FIGS. 10–11, the particles are not encapsulated by the binders, but are instead chemically bound or fused to the fiber at the interface between the particle and fiber. The particles and fibers of the present invention are not encapsulated with the binder. Moreover, the binder does not agglomerate the fibers together, and in many embodiments does not bind fibers to each other. Discrete individual particles retain their identity on the surface of the fibers, instead of being subsumed in a thermoplastic encasement around the fiber and particle.

XXII. Fiber Mixtures

The fibers of the present invention, such as fiber 600, can be mixed with other types of fibers, such as disclosed in U.S. Pat. No. 5,057,166. The latex coated fibers of that patent can be mixed with the fibers of the present invention to produce an absorbent product that has characteristics of both types of fibers.

XXIII. Additional Binder Characteristics

U.S. Pat. No. 3,903,889 discloses a process for adhering absorbent particles to pulp fibers using syrup, honey, and other polysaccharides such as dextrins. An essential requirement of these adhesive agents is that they must possess the property of being permanently pliable, and not rigidifying into a brittle film. The binders of the present invention, in contrast, are capable of functioning as a binder after solidifying into a rigid crystalline material. Even the binders of the present invention that do not rigidify into a solid (such as glycerin and PPG) are very hygroscopic, and can be present on fibers having a total water content of no more than 15%, or even 12%. This is in contrast to the adhesives such as honey and corn syrup disclosed in U.S. Pat. No. 3,903,889 that are not hygroscopic. Polysaccharides (such as corn syrup, honey and dextrins) are excluded as binders from some embodiments of the invention because they remain tacky upon drying. Tacky binders make processing and handling the binder-treated particles difficult. The polysaccharide polymers are also excluded from nonpolymeric embodiments of the binder of the present invention. Moreover, the nonpolymeric saccharides such as monosaccharides and disaccharides, lack some of the high viscosity and tacky-adhesive physical properties of polysaccharides such as corn syrup and honey. The nonpolymeric saccharides of the present invention may be solids, which avoid the viscosity and handling problems associated with corn syrup and honey.

As used in this application, a particle that is soluble in water will completely dissolve at least log of the particle in 300 ml water at 25° C. A particle that is sparingly soluble in the binder will completely dissolve no more than about 5 g of the particle in 300 ml of the binder at 25° C.

Some of the binders of the present invention are also water soluble. A binder that is soluble in water will completely dissolve at least log of the binder in 300 ml water at 25° C.

By applying binder to particles, the properties of the fibers are minimally impacted by the binder as the binder is substantially confined to the contact areas between the particles and fibers. Also, the quantities of binder required to adhere particles to the fibers is substantially reduced over the quantity required if the binder is applied to the fibers. For example, strong bonds exist even when 0.1% binder is applied to particles.

Having illustrated and described the principles of the invention in many preferred embodiments, it should be apparent to those skilled in the art that the invention can be modified in arrangement and detail without departing from such principles. We claim all modifications coming within the spirit and scope of the following claims.

We claim:

1. A method of binding superabsorbent particles to cellulose fibers with a nonpolymeric binder, comprising the steps of:
    providing cellulose fibers having a hydrogen bonding functionality;
    providing superabsorbent particles having a hydrogen bonding or a coordinate covalent bond forming functionality that have a nonpolymeric binder comprising propylene glycol applied thereto in the absence of the cellulose fibers, the propylene glycol being present on the superabsorbent particles in an amount from about 0.01 to 5.0% by weight based on the weight of the superabsorbent particles and being in an inactive state;
    activating the binder on the superabsorbent particles by providing heat to the superabsorbent particle; and
    binding at least a portion of the superabsorbent particles in particulate form carrying the activated binder to the cellulose fibers.

2. The method of claim 1, wherein the propylene glycol is present in an amount ranging from about 0.1 to 3% by weight based on the superabsorbent particles.

3. The method of claim 1, wherein the propylene glycol is present in an amount ranging from about 0.03 to. 1% by weight based on the superabsorbent particles.

4. A method of binding superabsorbent particles to cellulose fibers with a nonpolymeric binder, comprising the steps of:
    providing cellulose fibers having a hydrogen bonding functionality;
    providing superabsorbent particles having a hydrogen bonding or a coordinate covalent bond forming functionality that have a nonpolymeric binder comprising propylene glycol applied thereto in the absence of the cellulose fibers, the propylene glycol being present on the superabsorbent particles in an amount from about 0.01 to 5.0% by weight based on the weight of the superabsorbent particles and being in an inactive state;
    activating the binder on the superabsorbent particles by contacting an activating fluid with the superabsorbent particles; and
    binding at least a portion of the superabsorbent particles in particulate form carrying the activated binder to the cellulose fibers.

5. The method of claim 4, wherein the propylene glycol is present in an amount ranging from about 0.1 to 3% by weight based on the superabsorbent particles.

6. The method of claim 4, wherein the propylene glycol is present in an amount ranging from about 0.03 to 1% by weight based on the superabsorbent particles.

7. A method of binding superabsorbent particles to cellulose fibers with a nonpolymeric binder, comprising the steps of:
    providing cellulose fibers having a hydrogen bonding functionality;
    providing superabsorbent particles having a hydrogen bonding or a coordinate covalent bond forming functionality that have a nonpolymeric binder comprising trimethylene glycol applied thereto in the absence of the cellulose fibers, the trimethylene glycol being present on the superabsorbent particles in an amount from about 0.01 to 5.0% by weight based on the weight of the superabsorbent particles and being in an inactive state;
    activating the binder on the superabsorbent particles by providing heat to the superabsorbent particles; and
    binding at least a portion of the superabsorbent particles in particulate form carrying the activated binder to the cellulose fibers.

8. The method of claim 7, wherein the trimethylene glycol is present in an amount ranging from about 0.1 to 3% by weight based on the superabsorbent particles.

9. The method of claim 7, wherein the trimethylene glycol is present in an amount ranging from about 0.03 to 1% by weight based on the superabsorbent particles.

10. A method of binding superabsorbent particles to cellulose fibers with a nonpolymeric binder, comprising the steps of:
    providing cellulose fibers having a hydrogen bonding functionality;
    providing superabsorbent particles having a hydrogen bonding or a coordinate covalent bond forming functionality that have a nonpolymeric binder comprising trimethylene glycol applied thereto in the absence of the cellulose fibers, the trimethylene glycol being present on the superabsorbent particles in an amount from about 0.01 to 5.0% by weight based on the weight of the superabsorbent particles and being in an inactive state;
    activating the binder on the superabsorbent particles by contacting an activating fluid with the superabsorbent particles; and
    binding at least a portion of the superabsorbent particles in particulate form carrying the activated binder to the cellulose fibers.

11. The method of claim 10, wherein the trimethylene glycol is present in an amount ranging from about 0.1 to 3% by weight based on the superabsorbent particles.

12. The method of claim 10, wherein the trimethylene glycol is present in an amount ranging from about 0.03 to 1% by weight based on the superabsorbent particles.

13. A method of binding superabsorbent particles to cellulose fibers with a nonpolymeric binder, comprising the steps of:
    providing cellulose fibers having a hydrogen bonding functionality;
    providing superabsorbent particles having a hydrogen bonding or a coordinate covalent bond forming functionality that have a nonpolymeric binder comprising ethylene glycol applied thereto in the absence of the cellulose fibers, the ethylene glycol being present on the superabsorbent particles in an amount from about 0.01 to 5.0% by weight based on the weight of the superabsorbent particles and being in an inactive state;
    activating the binder on the superabsorbent particles by providing heat to the superabsorbent particles; and
    binding at least a portion of the superabsorbent particles in particulate form carrying the activated binder to the cellulose fibers.

14. The method of claim 13, wherein the ethylene glycol is present in an amount ranging from about 0.1 to 3% by weight based on the superabsorbent particles.

15. The method of claim 13, wherein the ethylene glycol is present in an amount ranging from about 0.03 to 1% by weight based on the superabsorbent particles.

16. A method of binding superabsorbent particles to cellulose fibers with a nonpolymeric binder, comprising the steps of:

provening cellulose fibers having a hydrogen bonding functionality;

providing superabsorbent particles having a hydrogen bonding or a coordinate covalent bond forming functionality that have a nonpolymeric binder comprising ethylene glycol applied thereto in the absence of the cellulose fibers, the ethylene glycol being present on the superabsorbent particles in an amount from about 0.01 to 5.0% by weight based on the weight of the superabsorbent particles and being in an inactive state;

activating the binder on the superabsorbent particles by contacting an activating fluid with the superabsorbent particles; and binding at least a portion of the superabsorbent particles in particulate form carrying the activated binder to the cellulose fibers.

17. The method of claim 16, wherein the ethylene glycol is present in an amount ranging from about 0.1 to 3% by weight based on the superabsorbent particles.

18. The method of claim 16, wherein the ethylene glycol is present in an amount ranging from about 0.03 to 1% by weight based on the superabsorbent particles.

19. A method of binding superabsorbent particles to cellulose fibers with a nonpolymeric binder, comprising the steps of:

providing cellulose fibers having a hydrogen bonding functionality;

providing superabsorbent particles having a hydrogen bonding or a coordinate covalent bond forming functionality that have a nonpolymeric binder comprising butylene glycol applied thereto in the absence of the cellulose fibers, the butylene glycol being present on the superabsorbent particles in an amount from about 0.01 to 5.0% by weight based on the weight of the superabsorbent particles and being in an inactive state;

activating the binder on the superabsorbent particles by providing heat to the superabsorbent particles; and binding at least a portion of the superabsorbent particles in particulate form carrying the activated binder to the cellulose fibers.

20. The method of claim 19, wherein the butylene glycol is present in an amount ranging from about 0.1 to 3% by weight based on the superabsorbent particles.

21. The method of claim 19, wherein the butylene glycol is present in an amount ranging from about 0.03 to 1% by weight based on the superabsorbent particles.

22. A method of binding superabsorbent particles to cellulose fibers with a nonpolymeric binder, comprising the steps of:

providing cellulose fibers having a hydrogen bonding functionality;

providing superabsorbent particles having a hydrogen bonding or a coordinate covalent bond forming functionality that have a nonpolymeric binder comprising butylene glycol applied thereto in the absence of the cellulose fibers, the butylene glycol being present on the superabsorbent particles in an amount from about 0.01 to 5.0% by weight based on the weight of the superabsorbent particles and being in an inactive state;

activating the binder on the superabsorbent particles by contacting an activating fluid with the superabsorbent particles; and binding at least a portion of the superabsorbent particles in particulate form carrying the activated binder to the cellulose fibers.

23. The method of claim 22, wherein the butylene glycol is present in an amount ranging from about 0.1 to 3% by weight based on the superabsorbent particles.

24. The method of claim 22, wherein the butylene glycol is present in an amount ranging from about 0.03 to 1% by weight based on the superabsorbent particles.

25. A method of binding superabsorbent particles to cellulose fibers with a nonpolymeric binder, comprising the steps of:

providing cellulose fibers having a hydrogen bonding functionality;

providing superabsorbent particles having a hydrogen bonding or a coordinate covalent bond forming functionality that have a nonpolymeric binder comprising dipropyplene glycol applied thereto in the absence of the cellulose fibers, the dipropyplene glycol being present on the superabsorbent particles in an amount from about 0.01 to 5.0% by weight based on the weight of the superabsorbent particles and being in an inactive state;

activating the binder on the superabsorbent particles by providing heat to the superabsorbent particles; and binding at least a portion of the superabsorbent particles in particulate form carrying the activated binder to the cellulose fibers.

26. The method of claim 25, wherein the dipropyplene glycol is present in an amount ranging from about 0.1 to 3% by weight based on the superabsorbent particles.

27. The method of claim 25, wherein the dipropyplene glycol is present in an amount ranging from about 0.03 to 1% by weight based on the superabsorbent particles.

28. A method of binding superabsorbent particles to cellulose fibers with a nonpolymeric binder, comprising the steps of:

providing cellulose fibers having a hydrogen bonding functionality;

providing superabsorbent particles having a hydrogen bonding or a coordinate covalent bond forming functionality that have a nonpolymeric binder comprising dipropyplene glycol applied thereto in the absence of the cellulose fibers, the dipropyplene glycol being present on the superabsorbent particles in an amount from about 0.01 to 5.0% by weight based on the weight of the superabsorbent particles and being in an inactive state;

activating the binder on the superabsorbent particles by contacting an activating fluid with the superabsorbent particles; and binding at least a portion of the superabsorbent particles in particulate form carrying the activated binder to the cellulose fibers.

29. The method of claim 28, wherein the dipropyplene glycol is present in an amount ranging from about 0.1 to 3% by weight based on the superabsorbent particles.

30. The method of claim 28, wherein the dipropyplene glycol is present in an amount ranging from about 0.03 to 1% by weight based on the superabsorbent particles.

* * * * *